(12) United States Patent
Ge et al.

(10) Patent No.: US 11,525,151 B2
(45) Date of Patent: Dec. 13, 2022

(54) GLUCOAMYLASES AND METHODS OF USE, THEREOF

(71) Applicant: DANISCO US INC, Palo Alto, CA (US)

(72) Inventors: Jing Ge, Shanghai (CN); Xiaogang Gu, Shanghai (CN); Helong Hao, Shanghai (CN); Karsten Matthias Kragh, Hoejbjerg (DK); Jinahua (Jalsen) Li, Shanghai (CN); Wenting Li, Wiltshire (GB); Zhongmei Tang, Shanghai (CN); Shukun Yu, Malmo (SE); Bo Zhong, Shanghai (CN); Kun Zhong, Shanghai (CN); Zhengzheng Zou, Shanghai (CN)

(73) Assignee: DANISCO US INC., Palo Alto, CA (US)

( * ) Notice: Subject to any disclaimer, the term of this patent is extended or adjusted under 35 U.S.C. 154(b) by 0 days.

(21) Appl. No.: 16/977,896

(22) PCT Filed: Mar. 6, 2019

(86) PCT No.: PCT/US2019/020876
§ 371 (c)(1),
(2) Date: Sep. 3, 2020

(87) PCT Pub. No.: WO2019/173424
PCT Pub. Date: Sep. 12, 2019

(65) Prior Publication Data
US 2021/0040523 A1 Feb. 11, 2021

(30) Foreign Application Priority Data
Mar. 9, 2018 (WO) ................ PCT/CN2018/078575

(51) Int. Cl.
*C12N 1/16* (2006.01)
*C12N 1/20* (2006.01)
*C12P 19/14* (2006.01)

(52) U.S. Cl.
CPC ................ *C12P 19/14* (2013.01); *C12N 1/16* (2013.01); *C12N 1/20* (2013.01); *C12P 2203/00* (2013.01)

(58) Field of Classification Search
None
See application file for complete search history.

(56) References Cited

U.S. PATENT DOCUMENTS 5,223,409 A 6/1993 Ladner et al.
6,022,725 A 2/2000 Fowler et al.
(Continued)

FOREIGN PATENT DOCUMENTS

CN 101310016 A 11/2008
CN 103667212 A 3/2014
(Continued)

OTHER PUBLICATIONS

UniProt Accession No. J4I862_9APHY, published Oct. 31, 2012 (Year: 2012).*
(Continued)

*Primary Examiner* — Richard C Ekstrom

(57) ABSTRACT

Described are methods for saccharifying starch-containing materials using a glucoamylase, methods for producing fermentation products, and fermentation products produced by the method thereof as well as methods for increasing starch digestibility in a ruminant using at least one of the glucoamylases described herein.

5 Claims, 1 Drawing Sheet

Specification includes a Sequence Listing.

| | FraGA1 | WcoGA1 | XP_002475369 | KZT67263 | US200900325240-1847 | KZT09226 | WO2016196202-0012 | US20170314003-0002 | GAD95639 | US20170306309-0023 | CAC28076 | TeGA | TrGA-2VN4_A | AnGA |
|---|---|---|---|---|---|---|---|---|---|---|---|---|---|---|
| FraGA1 | | 79.5 | 80 | 77.3 | 76.2 | 72.9 | 72.3 | 71.5 | 48.7 | 47.2 | 47.1 | 47 | 45.8 | 43.2 |
| WcoGA1 | 79.5 | | 82.2 | 79.6 | 79.5 | 75.5 | 71 | 69.9 | 50.3 | 48.2 | 48.6 | 48.3 | 46.3 | 45.7 |
| XP_002475369 | 80 | 82.2 | | 80 | 80.1 | 75.4 | 73.9 | 75.2 | 50 | 47.4 | 46.6 | 46.6 | 46.1 | 46.3 |
| KZT67263 | 77.3 | 79.6 | 80 | | 85 | 73.7 | 73.2 | 71.5 | 49.9 | 48.6 | 46.8 | 46.8 | 44.9 | 45.3 |
| US20090325240-1847 | 76.2 | 79.5 | 80.1 | 85 | | 73.2 | 74.3 | 71.2 | 51.1 | 50.3 | 49.4 | 49.5 | 48.1 | 47.9 |
| KZT09226 | 72.9 | 75.5 | 75.4 | 73.7 | 73.2 | | 68.8 | 68.4 | 49.7 | 47.6 | 46.8 | 46.7 | 44.9 | 46.4 |
| WO2016196202-0012 | 72.3 | 71 | 73.9 | 73.2 | 74.3 | 68.8 | | 80.6 | 51.6 | 50.6 | 49.9 | 49.8 | 49.6 | 45.2 |
| US20170314003-0002 | 71.5 | 69.9 | 75.2 | 71.5 | 71.2 | 68.4 | 80.6 | | 49.7 | 49.5 | 48.7 | 48.6 | 49.3 | 46.2 |
| GAD95639 | 48.7 | 50.3 | 50 | 49.9 | 51.1 | 49.7 | 51.6 | 49.7 | | 75.7 | 75.3 | 74.8 | 55.4 | 64.4 |
| US20170306309-0023 | 47.2 | 48.2 | 47.4 | 48.6 | 50.3 | 47.6 | 50.6 | 49.5 | 75.7 | | 95.1 | 94.6 | 57.7 | 61.3 |
| CAC28076 | 47.1 | 48.6 | 46.6 | 46.8 | 49.4 | 46.8 | 49.9 | 48.7 | 75.3 | 95.1 | | 99.5 | 57.4 | 60.8 |
| TeGA | 47 | 48.3 | 46.6 | 46.8 | 49.5 | 46.7 | 49.8 | 48.6 | 74.8 | 94.6 | 99.5 | | 57.2 | 60.6 |
| TrGA-2VN4_A | 45.8 | 46.3 | 46.1 | 44.9 | 48.1 | 44.9 | 49.6 | 49.3 | 55.4 | 57.7 | 57.4 | 57.2 | | 50.3 |
| AnGA | 43.2 | 45.7 | 46.3 | 45.3 | 47.9 | 46.4 | 45.2 | 46.2 | 64.4 | 61.3 | 60.8 | 60.6 | 50.3 | |

(56) References Cited

U.S. PATENT DOCUMENTS

| | | | |
|---|---|---|---|
| 2005/0037053 | A1 | 2/2005 | Isaksen et al. |
| 2008/0318284 | A1 | 12/2008 | Soong et al. |
| 2009/0325240 | A1 | 12/2009 | Daniell |
| 2011/0039308 | A1* | 2/2011 | Slupska ............... C12N 9/2428 435/101 |
| 2017/0136197 | A1 | 5/2017 | Christiansen et al. |
| 2017/0306309 | A1 | 10/2017 | Cramer et al. |
| 2017/0314003 | A1 | 11/2017 | Morant et al. |
| 2017/0321237 | A1 | 11/2017 | Fukuyama et al. |
| 2018/0080014 | A1* | 3/2018 | Miller ..................... C12P 19/14 |
| 2021/0040523 | A1* | 2/2021 | Ge ......................... C12P 19/02 |

FOREIGN PATENT DOCUMENTS

| | | |
|---|---|---|
| EP | 1951867 A2 | 8/2008 |
| KR | 1020010032489 | 4/2001 |
| WO | 9117243 A1 | 11/1991 |
| WO | 9206204 A1 | 4/1992 |
| WO | 1992012645 A1 | 8/1992 |
| WO | 9517413 A1 | 6/1995 |
| WO | 9522625 A1 | 8/1995 |
| WO | 1997016076 A1 | 5/1997 |
| WO | 0075296 A1 | 12/2000 |
| WO | 2007044968 A2 | 4/2007 |
| WO | 200806881 A1 | 1/2008 |
| WO | 2011063308 A2 | 5/2011 |
| WO | 2013189878 A1 | 12/2013 |
| WO | 2014060474 A1 | 4/2014 |
| WO | 2014177541 A2 | 11/2014 |
| WO | 2014202616 A2 | 12/2014 |
| WO | 2015065871 A1 | 5/2015 |
| WO | 2015128366 A2 | 9/2015 |
| WO | 2016138315 A1 | 9/2016 |
| WO | 2016196202 A1 | 12/2016 |

OTHER PUBLICATIONS

UniProt Accession No. A0A2H3JCA1_WOLCO, published Jan. 31, 2018 (Year: 2018).*

Geneseq Accession No. AAY23337, published Sep. 2, 1999 (Year: 1999).*

Carrasco et al., Purification and characterization of a novel cold adapted fungal glucoamylase, Microb Cell Fact (May 2017), 16:75, pp. 1-10.

Hua et al., A thermostable glucoamylase from *Bispora* sp. MEY-1 with stability over a broad pH range and significant starch hydrolysis capacity, PLoS One, vol. 9(11): e113581, Jul. 2014, 18 pages.

Nielsen et al., Cloning, heterologous expression, and enzymatic characterization of a thermostable glucoamylase from Talaromyces emersonii, Protein Expression and Purification 26 (Apr. 2002), 1-8.

Xian et al., Purification and biochemical characterization of a novel mesophilic glucoamylase fro Aspergillus tritici WZ99, International Journal of Biological Macromolecules, 107 (Sep. 2017), 1122-1130.

Xiao et al., Genome Mining for new α-Amylase and Glucoamylas Encoding Sequences and High Level Expression of a Glucoamylase from Talaromyces stipitatus for Potential Raw Starch Hydrolysis, Appl. Biochem. Biotechnol. (2014) 172:73-86.

UniParc Database Access No. UPI0002876966, Fibroporia radiculosa, XP002791204, 2012, 2 pgs.

UniParc Database Access No. UPI000BC159E9, *Wolfiporia cocos* (strain MD-104)(Brown rot fungus), XP002791205, 2017, 2 pgs.

PCT International Search Report and the Written Opinion of the International Searching Authority for International Application No. PCT/US2019/020876; Korsner, ISA/EP; dated May 24, 2019.

Beauchemin et al., A rationale for the development of feed enzyme products for ruminants., Can J. Anim. Sci. 84:23-36 (Dec. 2004).

* cited by examiner

|  | FraGA1 | WcoGA1 | XP_002475369 | KZT67263 | US20090325240-1847 | KZT09226 | WO2016196202-0012 | US20170314003-0002 | GAD95639 | US20170306309-0023 | CAC28076 | TeGA | TrGA-2VN4_A | AnGA |
|---|---|---|---|---|---|---|---|---|---|---|---|---|---|---|
| FraGA1 |  | 79.5 | 80 | 77.3 | 76.2 | 72.9 | 72.3 | 71.5 | 48.7 | 47.2 | 47.1 | 47 | 45.8 | 43.2 |
| WcoGA1 | 79.5 |  | 82.2 | 79.6 | 79.5 | 75.5 | 71 | 69.9 | 50.3 | 48.2 | 48.6 | 48.3 | 46.3 | 45.7 |
| XP_002475369 | 80 | 82.2 |  | 80 | 80.1 | 75.4 | 73.9 | 75.2 | 50 | 47.4 | 46.6 | 46.6 | 46.1 | 46.3 |
| KZT67263 | 77.3 | 79.6 | 80 |  | 85 | 73.7 | 73.2 | 71.5 | 49.9 | 48.6 | 46.8 | 46.8 | 44.9 | 45.3 |
| US20090325240-1847 | 76.2 | 79.5 | 80.1 | 85 |  | 73.2 | 74.3 | 71.2 | 51.1 | 50.3 | 49.4 | 49.5 | 48.1 | 47.9 |
| KZT09226 | 72.9 | 75.5 | 75.4 | 73.7 | 73.2 |  | 68.8 | 68.4 | 49.7 | 47.6 | 46.8 | 46.7 | 44.9 | 46.4 |
| WO2016196202-0012 | 72.3 | 71 | 73.9 | 73.2 | 74.3 | 68.8 |  | 80.6 | 51.6 | 50.6 | 49.9 | 49.8 | 49.6 | 45.2 |
| US20170314003-0002 | 71.5 | 69.9 | 75.2 | 71.5 | 71.2 | 68.4 | 80.6 |  | 49.7 | 49.5 | 48.7 | 48.6 | 49.3 | 46.2 |
| GAD95639 | 48.7 | 50.3 | 50 | 49.9 | 51.1 | 49.7 | 51.6 | 49.7 |  | 75.7 | 75.3 | 74.8 | 55.4 | 64.4 |
| US20170306309-0023 | 47.2 | 48.2 | 47.4 | 48.6 | 50.3 | 47.6 | 50.6 | 49.5 | 75.7 |  | 95.1 | 94.6 | 57.7 | 61.3 |
| CAC28076 | 47.1 | 48.6 | 46.6 | 46.8 | 49.4 | 46.8 | 49.9 | 48.7 | 75.3 | 95.1 |  | 99.5 | 57.4 | 60.8 |
| TeGA | 47 | 48.3 | 46.6 | 46.8 | 49.5 | 46.7 | 49.8 | 48.6 | 74.8 | 94.6 | 99.5 |  | 57.2 | 60.6 |
| TrGA-2VN4_A | 45.8 | 46.3 | 46.1 | 44.9 | 48.1 | 44.9 | 49.6 | 49.3 | 55.4 | 57.7 | 57.4 | 57.2 |  | 50.3 |
| AnGA | 43.2 | 45.7 | 46.3 | 45.3 | 47.9 | 46.4 | 45.2 | 46.2 | 64.4 | 61.3 | 60.8 | 60.6 | 50.3 |  |

SEQUENCE LISTING

```
<160> NUMBER OF SEQ ID NOS: 9

<210> SEQ ID NO 1
<211> LENGTH: 567
<212> TYPE: PRT
<213> ORGANISM: Fibroporia radiculosa

<400> SEQUENCE: 1

Met Leu Phe Leu Leu Ala Ala Leu Gly Leu Ala Cys Ser Ala Ala Ala
1               5                   10                  15

Gln Ser Thr Ser Val Ser Ala Tyr Ile Ala Ser Glu Ser Pro Val Ala
            20                  25                  30

Lys Ala Gly Val Leu Ala Asn Ile Gly Thr Glu Gly Ser Leu Ser Ser
        35                  40                  45
```

```
Gly Ala Tyr Ser Gly Val Val Ile Ala Ser Pro Ser Thr Val Asn Pro
    50              55              60

Asp Tyr Leu Tyr Thr Trp Val Arg Asp Ser Ser Leu Thr Phe Gln Ala
65              70              75              80

Leu Ile Asp Gln Tyr Val Tyr Gly Glu Asp Pro Thr Leu Arg Ser Leu
                85              90              95

Ile Asp Glu Phe Ile Thr Ala Glu Ser Ile Leu Gln Gln Thr Thr Asn
            100             105             110

Pro Ser Gly Thr Val Ser Thr Gly Gly Leu Gly Glu Pro Lys Phe Asn
        115             120             125

Ile Asn Glu Thr Ala Phe Thr Gly Pro Trp Gly Arg Pro Gln Arg Asp
    130             135             140

Gly Pro Ala Leu Arg Ser Thr Ala Ile Ile Thr Tyr Ala Thr Tyr Leu
145             150             155             160

Trp Asn Ser Gly Asn Thr Ser Tyr Val Ser Asp Ser Leu Trp Pro Ile
                165             170             175

Ile Glu Leu Asp Leu Asn Tyr Ile Ala Thr Tyr Trp Asn Phe Ser Thr
            180             185             190

Phe Asp Leu Trp Glu Glu Ile Asp Ser Ser Ser Phe Trp Thr Thr Ala
        195             200             205

Val Gln His Arg Ala Leu Arg Gln Gly Ile Thr Phe Ala Asn Leu Ile
    210             215             220

Gly Gln Thr Ser Pro Val Ser Asn Tyr Glu Thr Gln Ala Gly Asp Ile
225             230             235             240

Leu Cys Phe Leu Gln Thr Tyr Trp Asn Pro Thr Gly Asn Tyr Met Thr
                245             250             255

Ala Asn Thr Gly Gly Gly Arg Ser Gly Lys Asp Ser Asn Thr Val Leu
            260             265             270

Ala Ser Val His Thr Phe Asp Pro Asp Ala Gly Cys Asp Ser Thr Thr
        275             280             285

Phe Gln Pro Cys Ser Asp Lys Ala Leu Ser Asn Leu Lys Val Tyr Val
    290             295             300

Asp Ser Phe Arg Ser Leu Tyr Ala Ile Asn Asp Gly Ile Ala Ser Asp
305             310             315             320

Ala Ala Val Ala Thr Gly Arg Tyr Pro Glu Asp Val Tyr Tyr Gly Gly
                325             330             335

Asn Pro Trp Tyr Leu Cys Thr Phe Ala Val Ala Glu Gln Leu Tyr Asp
            340             345             350

Ala Leu Ile Val Trp Ser Ser Gln Gly Tyr Leu Glu Ile Thr Asp Leu
        355             360             365

Ser Leu Ala Phe Phe Gln Gln Phe Asp Ser Asp Val Gly Thr Gly Thr
    370             375             380

Tyr Asp Ser Gly Ser Ser Thr Tyr Ser Thr Leu Thr Ser Ala Ile Arg
385             390             395             400

Thr Phe Ala Asp Gly Phe Val Leu Thr Asn Ala Lys Tyr Thr Pro Thr
                405             410             415

Asn Gly Ser Leu Ser Glu Glu Tyr Thr Ser Ala Asp Gly Thr Pro Ile
            420             425             430

Ser Ala Tyr Asp Leu Thr Trp Ser Tyr Ala Ser Ala Leu Thr Val Phe
        435             440             445

Ala Ala Glu Ala Gly Thr Thr Tyr Gly Ser Trp Gly Ala Ala Gly Leu
    450             455             460
```

```
Thr Val Pro Ser Thr Cys Thr Ser Gly Val Ala Val Thr Phe Glu Val
465                 470                 475                 480

Asp Tyr Asp Thr Glu Tyr Gly Glu Asn Val Tyr Ile Thr Gly Ser Val
                485                 490                 495

Asn Ala Leu Glu Asn Trp Ser Ala Thr Asn Ala Leu Ile Met Ser Ala
            500                 505                 510

Ala Asp Tyr Pro Thr Trp Ser Ile Thr Val Tyr Leu Pro Pro Ser Thr
            515                 520                 525

Thr Ile Gln Tyr Lys Tyr Leu Thr Gln Tyr Asn Gly Glu Val Thr Trp
        530                 535                 540

Glu Asp Asp Pro Asn Asn Glu Ile Thr Thr Pro Ala Ser Gly Ser Met
545                 550                 555                 560

Thr Gln Val Asp Ser Trp His
                565

<210> SEQ ID NO 2
<211> LENGTH: 569
<212> TYPE: PRT
<213> ORGANISM: Wolfiporia cocos

<400> SEQUENCE: 2

Met Arg Leu Ser Leu Ala Ser Val Phe Ala Leu Ala Gly Gly Ala Leu
1               5                   10                  15

Ala Gln Thr Thr Ser Val Thr Ser Tyr Ile Ala Ser Glu Ser Pro Ile
            20                  25                  30

Ala Lys Ala Gly Val Leu Ala Asn Ile Gly Ala Asp Gly Ser Leu Ser
        35                  40                  45

Ser Gly Ala Tyr Ser Gly Ile Val Ile Ala Ser Pro Ser Thr Val Asn
50                  55                  60

Pro Asn Tyr Leu Tyr Thr Trp Thr Arg Asp Ser Ser Leu Thr Phe Met
65                  70                  75                  80

Glu Leu Ile Asn Gln Tyr Ile Tyr Gly Glu Asp Asp Thr Leu Arg Thr
                85                  90                  95

Leu Ile Asp Glu Phe Val Ser Ala Glu Ala Thr Leu Gln Gln Val Thr
            100                 105                 110

Asn Pro Ser Gly Thr Val Ser Thr Gly Gly Leu Gly Glu Pro Lys Phe
        115                 120                 125

Asn Ile Asn Glu Thr Ala Phe Thr Gly Pro Trp Gly Arg Pro Gln Arg
    130                 135                 140

Asp Gly Pro Ala Leu Arg Ala Thr Ala Ile Met Ala Tyr Ala Thr Tyr
145                 150                 155                 160

Leu Tyr Glu Asn Gly Asn Thr Ser Tyr Val Thr Asp Thr Leu Trp Pro
                165                 170                 175

Ile Ile Glu Leu Asp Leu Gly Tyr Val Ala Glu Tyr Trp Asn Glu Ser
            180                 185                 190

Thr Phe Asp Leu Trp Glu Glu Ile Asp Ser Ser Phe Phe Thr Thr
        195                 200                 205

Ala Val Gln His Arg Ala Leu Arg Ala Gly Val Thr Phe Ala Asn Leu
    210                 215                 220

Ile Gly Glu Thr Ser Asp Val Ser Asn Tyr Gln Glu Asn Ala Asp Asp
225                 230                 235                 240

Leu Leu Cys Phe Leu Gln Ser Tyr Trp Asn Pro Thr Gly Ser Tyr Val
                245                 250                 255

Thr Ala Asn Thr Gly Gly Gly Arg Ser Gly Lys Asp Ala Asn Thr Leu
            260                 265                 270
```

```
Leu Ala Ser Ile His Thr Phe Asp Pro Asp Ala Gly Cys Asn Ala Thr
            275                 280                 285

Thr Phe Gln Pro Cys Ser Asp Lys Ala Leu Ser Asn His Lys Val Tyr
290                 295                 300

Val Asp Ser Phe Arg Ser Leu Tyr Ala Ile Asn Asp Asp Ile Ser Ser
305                 310                 315                 320

Asp Ala Ala Val Ala Thr Gly Arg Tyr Pro Glu Asp Val Tyr Tyr Asn
                325                 330                 335

Gly Asn Pro Trp Tyr Leu Cys Thr Leu Ala Ala Ala Glu Gln Leu Tyr
                340                 345                 350

Asp Ser Leu Ile Val Trp Lys Ala Gln Gly Tyr Ile Glu Val Thr Ser
                355                 360                 365

Leu Ser Leu Ala Phe Phe Gln Gln Phe Asp Ala Ser Val Ser Ala Gly
370                 375                 380

Thr Tyr Asp Ser Ser Ser Asp Thr Tyr Thr Thr Leu Leu Asp Ala Val
385                 390                 395                 400

Gln Thr Tyr Ala Asp Gly Phe Val Leu Met Val Ala Gln Tyr Thr Pro
                405                 410                 415

Ala Asn Gly Ser Leu Ser Glu Tyr Ala Lys Ala Asp Gly Ser Pro
                420                 425                 430

Thr Ser Ala Tyr Asp Leu Thr Trp Ser Phe Ala Ala Leu Thr Ala
                435                 440                 445

Phe Ala Ala Arg Asp Gly Lys Thr Tyr Gly Ser Trp Gly Ala Ala Asp
450                 455                 460

Leu Ser Ser Thr Cys Ser Gly Ser Thr Asp Thr Val Ala Val Thr Phe
465                 470                 475                 480

Glu Val Gln Tyr Asp Thr Gln Tyr Gly Glu Asn Leu Tyr Ile Thr Gly
                485                 490                 495

Ser Val Ser Gln Leu Glu Asp Trp Ser Ala Asp Ala Leu Ile Met
                500                 505                 510

Ser Ser Ala Asp Tyr Pro Thr Trp Ser Ile Thr Val Asp Leu Pro Pro
                515                 520                 525

Ser Thr Leu Ile Gln Tyr Lys Tyr Leu Thr Lys Tyr Asn Gly Asp Val
                530                 535                 540

Thr Trp Glu Asp Asp Pro Asn Asn Glu Ile Thr Thr Pro Ala Ser Gly
545                 550                 555                 560

Ser Tyr Thr Gln Val Asp Ser Trp His
                565

<210> SEQ ID NO 3
<211> LENGTH: 618
<212> TYPE: PRT
<213> ORGANISM: Talaromyces emersonii

<400> SEQUENCE: 3

Met Ala Ser Leu Val Ala Gly Ala Leu Cys Ile Leu Gly Leu Thr Pro
1               5                   10                  15

Ala Ala Phe Ala Arg Ala Pro Val Ala Ala Arg Ala Thr Gly Ser Leu
                20                  25                  30

Asp Ser Phe Leu Ala Thr Glu Thr Pro Ile Ala Leu Gln Gly Val Leu
            35                  40                  45

Asn Asn Ile Gly Pro Asn Gly Ala Asp Val Ala Gly Ala Ser Ala Gly
        50                  55                  60

Ile Val Val Ala Ser Pro Ser Arg Ser Asp Pro Asn Tyr Phe Tyr Ser
```

-continued

```
             65                  70                  75                  80
Trp Thr Arg Asp Ala Ala Leu Thr Ala Lys Tyr Leu Val Asp Ala Phe
                     85                  90                  95
Asn Arg Gly Asn Lys Asp Leu Glu Gln Thr Ile Gln Gln Tyr Ile Ser
                100                 105                 110
Ala Gln Ala Lys Val Gln Thr Ile Ser Asn Pro Ser Gly Asp Leu Ser
                115                 120                 125
Thr Gly Gly Leu Gly Glu Pro Lys Phe Asn Val Asn Glu Thr Ala Phe
                130                 135                 140
Thr Gly Pro Trp Gly Arg Pro Gln Arg Asp Gly Pro Ala Leu Arg Ala
145                 150                 155                 160
Thr Ala Leu Ile Ala Tyr Ala Asn Tyr Leu Ile Asp Asn Gly Glu Ala
                165                 170                 175
Ser Thr Ala Asp Glu Ile Ile Trp Pro Ile Val Gln Asn Asp Leu Ser
                180                 185                 190
Tyr Ile Thr Gln Tyr Trp Asn Ser Ser Thr Phe Asp Leu Trp Glu Glu
                195                 200                 205
Val Glu Gly Ser Ser Phe Phe Thr Thr Ala Val Gln His Arg Ala Leu
                210                 215                 220
Val Glu Gly Asn Ala Leu Ala Thr Arg Leu Asn His Thr Cys Ser Asn
225                 230                 235                 240
Cys Val Ser Gln Ala Pro Gln Val Leu Cys Phe Leu Gln Ser Tyr Trp
                245                 250                 255
Thr Gly Ser Tyr Val Leu Ala Asn Phe Gly Gly Ser Gly Arg Ser Gly
                260                 265                 270
Lys Asp Val Asn Ser Ile Leu Gly Ser Ile His Thr Phe Asp Pro Ala
                275                 280                 285
Gly Gly Cys Asp Asp Ser Thr Phe Gln Pro Cys Ser Ala Arg Ala Leu
                290                 295                 300
Ala Asn His Lys Val Val Thr Asp Ser Phe Arg Ser Ile Tyr Ala Ile
305                 310                 315                 320
Asn Ser Gly Ile Ala Glu Gly Ser Ala Val Ala Val Gly Arg Tyr Pro
                325                 330                 335
Glu Asp Val Tyr Gln Gly Gly Asn Pro Trp Tyr Leu Ala Thr Ala Ala
                340                 345                 350
Ala Ala Glu Gln Leu Tyr Asp Ala Ile Tyr Gln Trp Lys Lys Ile Gly
                355                 360                 365
Ser Ile Ser Ile Thr Asp Val Ser Leu Pro Phe Phe Gln Asp Ile Tyr
                370                 375                 380
Pro Ser Ala Ala Val Gly Thr Tyr Asn Ser Gly Ser Thr Thr Phe Asn
385                 390                 395                 400
Asp Ile Ile Ser Ala Val Gln Thr Tyr Gly Asp Gly Tyr Leu Ser Ile
                405                 410                 415
Val Glu Lys Tyr Thr Pro Ser Asp Gly Ser Leu Thr Glu Gln Phe Ser
                420                 425                 430
Arg Thr Asp Gly Thr Pro Leu Ser Ala Ser Ala Leu Thr Trp Ser Tyr
                435                 440                 445
Ala Ser Leu Leu Thr Ala Ser Ala Arg Arg Gln Ser Val Val Pro Ala
                450                 455                 460
Ser Trp Gly Glu Ser Ser Ala Ser Ser Val Leu Ala Val Cys Ser Ala
465                 470                 475                 480
Thr Ser Ala Thr Gly Pro Tyr Ser Thr Ala Thr Asn Thr Val Trp Pro
                485                 490                 495
```

```
Ser Ser Gly Ser Gly Ser Ser Thr Thr Thr Ser Ser Ala Pro Cys Thr
            500                 505                 510

Thr Pro Thr Ser Val Ala Val Thr Phe Asp Glu Ile Val Ser Thr Ser
        515                 520                 525

Tyr Gly Glu Thr Ile Tyr Leu Ala Gly Ser Ile Pro Glu Leu Gly Asn
    530                 535                 540

Trp Ser Thr Ala Ser Ala Ile Pro Leu Arg Ala Asp Ala Tyr Thr Asn
545                 550                 555                 560

Ser Asn Pro Leu Trp Tyr Val Thr Val Asn Leu Pro Pro Gly Thr Ser
                565                 570                 575

Phe Glu Tyr Lys Phe Phe Lys Asn Gln Thr Asp Gly Thr Ile Val Trp
            580                 585                 590

Glu Asp Asp Pro Asn Arg Ser Tyr Thr Val Pro Ala Tyr Cys Gly Gln
        595                 600                 605

Thr Thr Ala Ile Leu Asp Asp Ser Trp Gln
    610                 615

<210> SEQ ID NO 4
<211> LENGTH: 1704
<212> TYPE: DNA
<213> ORGANISM: Fibroporia radiculosa

<400> SEQUENCE: 4
atgctcttcc tcctcgctgc tctgggcctc gcttgtagcg ctgctgccca atccacttcc      60
gtctccgctt acatcgccag cgagagcccc gttgccaaag ccggtgttct ggctaacatt     120
ggcactgaag gtagcctgag ctccggtgcc tactccggcg ttgtcatcgc ctcccccagc     180
accgtcaacc ctgactacct ctatacttgg gttcgcgact ccagcctcac tttccaagcc     240
ctgattgacc agtacgttta cggcgaggac cccacccctcc gaagcctgat cgacgagttc     300
attaccgctg agtccatcct gcagcaaact accaacccca gcggcaccgt tagcaccggc     360
ggtctgggcg agcccaagtt caacatcaat gagactgcct taccggtcc ctggggccga     420 ccccaacgcg acgtcctgc cctccgcagc actgccatca ttacttatgc cacctacctg     480
tggaactccg gtaacaccctc ctacgtttcc gattccctct ggcccatcat cgaactcgac     540
ctgaattaca ttgctaccta ctggaatttc tccacttttg atctgtggga agagattgac     600
tcctccagct ctggaccac tgccgttcag catcgagccc tgcgccaggg tatcaccttc     660
gctaatctga ttggccagac cagccctgtc agcaactatg agacccaagc cggcgatatc     720 ctctgttttcc tccaaaccta ttggaatcct accggcaact acatgaccgc caatactggc     780
ggtggtcgaa gcggcaagga ctccaacacc gttctcgctt ccgttcatac cttcgatccc     840
gatgccggct gtgatagcac tacttttcaa ccttgctccg acaaggccct gagcaacctc     900
aaggtctacg tcgactcctt tcgcagcctg tacgccatca cgacggtat tgcctccgac     960 gctgccgtcg ccaccggccg ctatcctgag gacgtctact acggcggtaa ccctggtac    1020 ctctgcacct ttgctgtcgc cgaacaactc tacgacgccc tcatcgtctg gagcagccag    1080
ggctatctcg aaatcactga cctcagcctg gccttcttcc agcagtttga ttccgatgtc    1140
ggtactggca cctacgacag cggctccagc acttactcca ctctcacctc cgccatccga    1200
acttttgctg atggcttcgt tctgaccaac gccaaataca cccctaccaa tggttccctg    1260
tccgaggagt acaccagcgc cgatggcact cctatctccg cctatgacct gacctggagc    1320
tacgcctccg ctctgaccgt ctttgccgcc gaggccggca ccacttacgg ctcctggggt    1380
```

```
gctgctggcc tgactgtccc tagcacctgc actagcggcg tcgctgttac tttcgaggtc    1440
gattacgaca ccgagtatgg cgaaaacgtc tatatcaccg gttccgtcaa tgccctggaa    1500
aattggtccg ccactaatgc tctgattatg tccgccgctg actatcccac ctggtccatc    1560
accgtttacc tgcccccctc caccaccatt cagtataagt atctcaccca gtacaacggc    1620
gaagtcactt gggaggacga ccctaacaac gagattacta cccctgctag cggttccatg    1680
acccaggttg acagctggca ctaa                                           1704
```

<210> SEQ ID NO 5
<211> LENGTH: 1710
<212> TYPE: DNA
<213> ORGANISM: Wolfiporia cocos

<400> SEQUENCE: 5

```
atgcgactga gcctggcctc cgttttgct ctcgccggtg gtgccctcgc ccagaccact      60
agcgtcacct cctacattgc tagcgaaagc cccattgcca agccggtgt tctcgctaac     120 attggcgctg acgctcccct gagctccggt gcttattccg gcattgttat cgccagcccc    180
tccaccgtta accctaacta tctctatacc tggactcgcg actccagcct gaccttcatg    240
gaactgatca ccagtacat ctacggcgag gacgatactc tgcgaactct gattgatgag     300 ttcgttttccg ctgaagccac cctccaacag gtcactaatc ctagcggcac tgtctccact    360
ggtggcctcg cgagcccaa gttcaacatc aacgagactg cttttactgg tccctggggc     420
cgaccccaac gcgatggccc tgccctgcgc gctactgcta tcatggccta tgccacctac    480
ctgtatgaaa acgtaatac tagctatgtt actgacaccc tctggcccat cattgaactc     540
gacctcggtt acgtcgccga atattggaac gaaagcacct ttgatctctg ggaggaaatc    600
gacagcagct cctttttcac taccgctgtt cagcaccgcg ctctccgcgc tggcgttacc    660
ttcgccaatc tcatcggtga ccagcgac gtcagcaact accaggaaaa tgccgacgac      720
ctcctctgct tcctccaaag ctactggaac cccactggca gctacgtcac tgctaacact    780
ggcggtggtc gaagcggcaa ggacgccaac actctcctgg ctagcatcca cacttcgat    840 cccgacgctg gctgcaacgc cactacttt caaccctgtt ccgacaaagc cctcagcaat    900
cacaaggtct acgttgactc cttccgcagc ctctacgcca tcaatgacga cattagcagc   960
gatgccgctg tcgctaccgg ccgatacct gaggatgtct actacaacgg caaccccctgg 1020 tacctctgta ccctggccgc tgctgagcaa ctctacgact ccctcatcgt ctggaaggcc   1080
caaggctaca tcgaagtcac cagcctcagc ctcgcctttt ttcaacagtt cgatgcttcc   1140
gttagcgccg gtacttatga ttccagctcc gacacctaca ccaccctgct cgacgccgtt   1200
cagacctatg ctgatggctt cgtcctgatg gtcgctcagt acacccctgc caacggttcc   1260
ctctccgagc agtacgccaa ggccgatggc agccccactt ccgcctacga cctgacttgg   1320
tcctttgctg ctgccctcac cgccttcgct gcccgcgacg gcaaaaccta tggtagctgg   1380
ggtgccgccg atctctccag cacctgcagc ggttccaccg acactgtcgc cgtcactttc   1440
gaggtccagt acgacaccca atatggtgaa atctgtaca ttaccggcag cgtctcccag    1500
ctcgaggatt ggagcgctga tgatgctctc atcatgtcca cgccgacta tcccacctgg   1560 tccatcaccg tcgatctgcc ccctagcacc ctgatccaat acaaatacct caccaagtat   1620
aacggcgatg tcacctggga agacgatccc aacaacgaaa ttaccactcc tgcctccggc   1680
tcctataccc aggttgacag ctggcactaa                                    1710
```

<210> SEQ ID NO 6
<211> LENGTH: 1857
<212> TYPE: DNA
<213> ORGANISM: Talaromyces emersonii

<400> SEQUENCE: 6

| | |
|---|---|
| atggcctccc tggttgctgg tgctctgtgc atcctcggcc tgacccctgc cgccttcgcc | 60 |
| cgagccccccg tcgctgcccg cgccactggc agcctcgaca gcttcctcgc caccgagacc | 120 |
| cctatcgccc tccagggcgt tctgaacaac atcggtccca acggcgctga cgtcgccggt | 180 |
| gctagcgccg gtatcgtcgt tgccagccct agccgatccg accccaacta cttctacagc | 240 |
| tggacccgcg acgccgctct caccgctaag tacctggtcg acgccttcaa tcgcggcaac | 300 |
| aaagacctcg agcaaaccat ccagcagtac atctccgctc aggccaaggt ccagaccatt | 360 |
| tccaacccca gcggcgatct gagcactggc ggcctgggcg agcccaagtt caacgtcaat | 420 |
| gagaccgctt tcactggccc ctggggccga cctcaacgcg atggccctgc tctccgagcc | 480 |
| accgccctca tcgcctatgc taactacctg atcgacaacg gtgaggccag cactgccgac | 540 |
| gagatcatct ggcccatcgt ccaaaatgac ctcagctaca tcacccaata ctggaactcc | 600 |
| agcacctttg acctgtggga ggaggtcgag ggctccagct tcttcaccac tgctgttcag | 660 |
| caccgcgccc tcgttgaggg taatgccctg gccacccgac tcaatcacac ttgctccaac | 720 |
| tgcgtcagcc aggccccccca ggtcctctgc tttctccaga gctactggac cggcagctac | 780 |
| gtcctggcca actttggtgg cagcggccga agcggcaagg acgtcaacag catcctgggt | 840 |
| tccatccaca ccttcgaccc cgctggcggt tgcgacgact ccactttcca gccttgcagc | 900 |
| gctcgcgctc tcgccaacca aaggtcgtc accgattcct tccgctccat ctacgccatc | 960 |
| aattccggca tcgccgaggg tagcgctgtt gctgtcggcc gctaccccga ggacgtctac | 1020 |
| caaggcggca atccctggta tctcgctact gccgctgccg ccgagcagct ctatgacgct | 1080 |
| atctatcagt ggaaaaagat cggtagcatc agcattaccg acgtcagcct ccccttcttc | 1140 |
| caggacatct accctccgc cgctgttggc acctacaatt ccggctccac caccttcaac | 1200 |
| gacatcatca gcgccgtcca gacttatggc gacggctacc tgagcattgt cgagaagtac | 1260 |
| acccccagcg atggcagcct caccgagcaa ttcagccgca ccgacggcac ccccctgtcc | 1320 |
| gcttccgccc tcacctggag ctacgcttcc ctgctcaccg cctccgctcg ccgccagagc | 1380 |
| gtcgttcccg ctagctgggg cgagagcagc gccagctccg tcctggccgt ctgctccgct | 1440 |
| actagcgcca ccggcccctca ctccactgcc accaacaccg tttggccttc cagcggctcc | 1500 |
| ggcagctcca ctaccacctc cagcgcccct tgcaccaccc ctaccagcgt cgccgtcacc | 1560 |
| ttcgacgaga tcgtcagcac cagctacggc gagaccatct atctggctgg cagcatcccc | 1620 |
| gagctgggca attggtccac cgccagcgct attcctctgc gcgctgacgc ctacactaat | 1680 |
| agcaaccctc tgtggtatgt caccgttaac ctccctcccg gcactagctt tgagtataag | 1740 |
| tttttcaaga accagaccga tggtactatt gtctgggagg acgaccccaa ccgatcctac | 1800 |
| accgtccccg cctactgcgg tcagactacc gctatcctcg acgattcctg gcagtaa | 1857 |

<210> SEQ ID NO 7
<211> LENGTH: 551
<212> TYPE: PRT
<213> ORGANISM: Fibroporia radiculosa

<400> SEQUENCE: 7

Gln Ser Thr Ser Val Ser Ala Tyr Ile Ala Ser Glu Ser Pro Val Ala
1               5                   10                  15

```
Lys Ala Gly Val Leu Ala Asn Ile Gly Thr Glu Gly Ser Leu Ser Ser
            20                  25                  30

Gly Ala Tyr Ser Gly Val Val Ile Ala Ser Pro Ser Thr Val Asn Pro
            35                  40              45

Asp Tyr Leu Tyr Thr Trp Val Arg Asp Ser Ser Leu Thr Phe Gln Ala
 50                      55                  60

Leu Ile Asp Gln Tyr Val Tyr Gly Glu Asp Pro Thr Leu Arg Ser Leu
 65                  70                  75                  80

Ile Asp Glu Phe Ile Thr Ala Glu Ser Ile Leu Gln Gln Thr Thr Asn
                 85                  90                  95

Pro Ser Gly Thr Val Ser Thr Gly Leu Gly Glu Pro Lys Phe Asn
                100                 105                 110

Ile Asn Glu Thr Ala Phe Thr Gly Pro Trp Gly Arg Pro Gln Arg Asp
            115                 120                 125

Gly Pro Ala Leu Arg Ser Thr Ala Ile Ile Thr Tyr Ala Thr Tyr Leu
130                 135                 140

Trp Asn Ser Gly Asn Thr Ser Tyr Val Ser Asp Ser Leu Trp Pro Ile
145                 150                 155                 160

Ile Glu Leu Asp Leu Asn Tyr Ile Ala Thr Tyr Trp Asn Phe Ser Thr
                165                 170                 175

Phe Asp Leu Trp Glu Glu Ile Asp Ser Ser Ser Phe Trp Thr Thr Ala
            180                 185                 190

Val Gln His Arg Ala Leu Arg Gln Gly Ile Thr Phe Ala Asn Leu Ile
            195                 200                 205

Gly Gln Thr Ser Pro Val Ser Asn Tyr Glu Thr Gln Ala Gly Asp Ile
            210                 215                 220

Leu Cys Phe Leu Gln Thr Tyr Trp Asn Pro Thr Gly Asn Tyr Met Thr
225                 230                 235                 240

Ala Asn Thr Gly Gly Gly Arg Ser Gly Lys Asp Ser Asn Thr Val Leu
                245                 250                 255

Ala Ser Val His Thr Phe Asp Pro Asp Ala Gly Cys Asp Ser Thr Thr
            260                 265                 270

Phe Gln Pro Cys Ser Asp Lys Ala Leu Ser Asn Leu Lys Val Tyr Val
            275                 280                 285

Asp Ser Phe Arg Ser Leu Tyr Ala Ile Asn Asp Gly Ile Ala Ser Asp
 290                 295                 300

Ala Ala Val Ala Thr Gly Arg Tyr Pro Glu Asp Val Tyr Tyr Gly Gly
305                 310                 315                 320

Asn Pro Trp Tyr Leu Cys Thr Phe Ala Val Ala Glu Gln Leu Tyr Asp
                325                 330                 335

Ala Leu Ile Val Trp Ser Ser Gln Gly Tyr Leu Glu Ile Thr Asp Leu
            340                 345                 350

Ser Leu Ala Phe Phe Gln Gln Phe Asp Ser Asp Val Gly Thr Gly Thr
            355                 360                 365

Tyr Asp Ser Gly Ser Ser Thr Tyr Ser Thr Leu Thr Ser Ala Ile Arg
 370                 375                 380

Thr Phe Ala Asp Gly Phe Val Leu Thr Asn Ala Lys Tyr Thr Pro Thr
385                 390                 395                 400

Asn Gly Ser Leu Ser Glu Glu Tyr Thr Ser Ala Asp Gly Thr Pro Ile
                405                 410                 415

Ser Ala Tyr Asp Leu Thr Trp Ser Tyr Ala Ser Ala Leu Thr Val Phe
            420                 425                 430
```

```
Ala Ala Glu Ala Gly Thr Thr Tyr Gly Ser Trp Gly Ala Ala Gly Leu
            435                 440                 445

Thr Val Pro Ser Thr Cys Thr Ser Gly Val Ala Val Thr Phe Glu Val
450                 455                 460

Asp Tyr Asp Thr Glu Tyr Gly Glu Asn Val Tyr Ile Thr Gly Ser Val
465                 470                 475                 480

Asn Ala Leu Glu Asn Trp Ser Ala Thr Asn Ala Leu Ile Met Ser Ala
                485                 490                 495

Ala Asp Tyr Pro Thr Trp Ser Ile Thr Val Tyr Leu Pro Pro Ser Thr
            500                 505                 510

Thr Ile Gln Tyr Lys Tyr Leu Thr Gln Tyr Asn Gly Glu Val Thr Trp
        515                 520                 525

Glu Asp Asp Pro Asn Asn Glu Ile Thr Thr Pro Ala Ser Gly Ser Met
530                 535                 540

Thr Gln Val Asp Ser Trp His
545                 550

<210> SEQ ID NO 8
<211> LENGTH: 552
<212> TYPE: PRT
<213> ORGANISM: Wolfiporia cocos

<400> SEQUENCE: 8

Gln Thr Thr Ser Val Thr Ser Tyr Ile Ala Ser Glu Ser Pro Ile Ala
1               5                   10                  15

Lys Ala Gly Val Leu Ala Asn Ile Gly Ala Asp Gly Ser Leu Ser Ser
            20                  25                  30

Gly Ala Tyr Ser Gly Ile Val Ile Ala Ser Pro Ser Thr Val Asn Pro
        35                  40                  45

Asn Tyr Leu Tyr Thr Trp Thr Arg Asp Ser Ser Leu Thr Phe Met Glu
50                  55                  60

Leu Ile Asn Gln Tyr Ile Tyr Gly Glu Asp Asp Thr Leu Arg Thr Leu
65                  70                  75                  80

Ile Asp Glu Phe Val Ser Ala Glu Ala Thr Leu Gln Gln Val Thr Asn
                85                  90                  95

Pro Ser Gly Thr Val Ser Thr Gly Gly Leu Gly Glu Pro Lys Phe Asn
            100                 105                 110

Ile Asn Glu Thr Ala Phe Thr Gly Pro Trp Gly Arg Pro Gln Arg Asp
        115                 120                 125

Gly Pro Ala Leu Arg Ala Thr Ala Ile Met Ala Tyr Ala Thr Tyr Leu
130                 135                 140

Tyr Glu Asn Gly Asn Thr Ser Tyr Val Thr Asp Thr Leu Trp Pro Ile
145                 150                 155                 160

Ile Glu Leu Asp Leu Gly Tyr Val Ala Glu Tyr Trp Asn Glu Ser Thr
                165                 170                 175

Phe Asp Leu Trp Glu Glu Ile Asp Ser Ser Phe Phe Thr Thr Ala
            180                 185                 190

Val Gln His Arg Ala Leu Arg Ala Gly Val Thr Phe Ala Asn Leu Ile
        195                 200                 205

Gly Glu Thr Ser Asp Val Ser Asn Tyr Gln Glu Asn Ala Asp Asp Leu
210                 215                 220

Leu Cys Phe Leu Gln Ser Tyr Trp Asn Pro Thr Gly Ser Tyr Val Thr
225                 230                 235                 240

Ala Asn Thr Gly Gly Gly Arg Ser Gly Lys Asp Ala Asn Thr Leu Leu
                245                 250                 255
```

```
Ala Ser Ile His Thr Phe Asp Pro Asp Ala Gly Cys Asn Ala Thr Thr
            260                 265                 270

Phe Gln Pro Cys Ser Asp Lys Ala Leu Ser Asn His Lys Val Tyr Val
        275                 280                 285

Asp Ser Phe Arg Ser Leu Tyr Ala Ile Asn Asp Ile Ser Ser Asp
    290                 295                 300

Ala Ala Val Ala Thr Gly Arg Tyr Pro Glu Asp Val Tyr Tyr Asn Gly
305                 310                 315                 320

Asn Pro Trp Tyr Leu Cys Thr Leu Ala Ala Glu Gln Leu Tyr Asp
                325                 330                 335

Ser Leu Ile Val Trp Lys Ala Gln Gly Tyr Ile Glu Val Thr Ser Leu
                340                 345                 350

Ser Leu Ala Phe Phe Gln Gln Phe Asp Ala Ser Val Ser Ala Gly Thr
                355                 360                 365

Tyr Asp Ser Ser Ser Asp Thr Tyr Thr Thr Leu Leu Asp Ala Val Gln
            370                 375                 380

Thr Tyr Ala Asp Gly Phe Val Leu Met Val Ala Gln Tyr Thr Pro Ala
385                 390                 395                 400

Asn Gly Ser Leu Ser Glu Gln Tyr Ala Lys Ala Asp Gly Ser Pro Thr
                405                 410                 415

Ser Ala Tyr Asp Leu Thr Trp Ser Phe Ala Ala Leu Thr Ala Phe
            420                 425                 430

Ala Ala Arg Asp Gly Lys Thr Tyr Gly Ser Trp Gly Ala Ala Asp Leu
                435                 440                 445

Ser Ser Thr Cys Ser Gly Ser Thr Asp Thr Val Ala Val Thr Phe Glu
450                 455                 460

Val Gln Tyr Asp Thr Gln Tyr Gly Glu Asn Leu Tyr Ile Thr Gly Ser
465                 470                 475                 480

Val Ser Gln Leu Glu Asp Trp Ser Ala Asp Asp Ala Leu Ile Met Ser
                485                 490                 495

Ser Ala Asp Tyr Pro Thr Trp Ser Ile Thr Val Asp Leu Pro Pro Ser
                500                 505                 510

Thr Leu Ile Gln Tyr Lys Tyr Leu Thr Lys Tyr Asn Gly Asp Val Thr
                515                 520                 525

Trp Glu Asp Asp Pro Asn Asn Glu Ile Thr Pro Ala Ser Gly Ser
530                 535                 540

Tyr Thr Gln Val Asp Ser Trp His
545                 550
```

<210> SEQ ID NO 9
<211> LENGTH: 591
<212> TYPE: PRT
<213> ORGANISM: Talaromyces emersonii

<400> SEQUENCE: 9

```
Ala Thr Gly Ser Leu Asp Ser Phe Leu Ala Thr Glu Thr Pro Ile Ala
1               5                   10                  15

Leu Gln Gly Val Leu Asn Asn Ile Gly Pro Asn Gly Ala Asp Val Ala
            20                  25                  30

Gly Ala Ser Ala Gly Ile Val Val Ala Ser Pro Ser Arg Ser Asp Pro
        35                  40                  45

Asn Tyr Phe Tyr Ser Trp Thr Arg Asp Ala Ala Leu Thr Ala Lys Tyr
    50                  55                  60

Leu Val Asp Ala Phe Asn Arg Gly Asn Lys Asp Leu Glu Gln Thr Ile
```

```
                65                  70                  75                  80
        Gln Gln Tyr Ile Ser Ala Gln Ala Lys Val Gln Thr Ile Ser Asn Pro
                            85                  90                  95

Ser Gly Asp Leu Ser Thr Gly Gly Leu Gly Glu Pro Lys Phe Asn Val
                    100                 105                 110

Asn Glu Thr Ala Phe Thr Gly Pro Trp Gly Arg Pro Gln Arg Asp Gly
                    115                 120                 125

Pro Ala Leu Arg Ala Thr Ala Leu Ile Ala Tyr Ala Asn Tyr Leu Ile
                    130                 135                 140

Asp Asn Gly Glu Ala Ser Thr Ala Asp Glu Ile Ile Trp Pro Ile Val
        145                 150                 155                 160

Gln Asn Asp Leu Ser Tyr Ile Thr Gln Tyr Trp Asn Ser Ser Thr Phe
                        165                 170                 175

Asp Leu Trp Glu Glu Val Glu Gly Ser Ser Phe Phe Thr Thr Ala Val
                        180                 185                 190

Gln His Arg Ala Leu Val Glu Gly Asn Ala Leu Ala Thr Arg Leu Asn
                        195                 200                 205

His Thr Cys Ser Asn Cys Val Ser Gln Ala Pro Gln Val Leu Cys Phe
                    210                 215                 220

Leu Gln Ser Tyr Trp Thr Gly Ser Tyr Val Leu Ala Asn Phe Gly Gly
        225                 230                 235                 240

Ser Gly Arg Ser Gly Lys Asp Val Asn Ser Ile Leu Gly Ser Ile His
                        245                 250                 255

Thr Phe Asp Pro Ala Gly Gly Cys Asp Asp Ser Thr Phe Gln Pro Cys
                    260                 265                 270

Ser Ala Arg Ala Leu Ala Asn His Lys Val Val Thr Asp Ser Phe Arg
                    275                 280                 285

Ser Ile Tyr Ala Ile Asn Ser Gly Ile Ala Glu Gly Ser Ala Val Ala
                    290                 295                 300

Val Gly Arg Tyr Pro Glu Asp Val Tyr Gln Gly Gly Asn Pro Trp Tyr
        305                 310                 315                 320

Leu Ala Thr Ala Ala Ala Glu Gln Leu Tyr Asp Ala Ile Tyr Gln
                        325                 330                 335

Trp Lys Lys Ile Gly Ser Ile Ser Ile Thr Asp Val Ser Leu Pro Phe
                        340                 345                 350

Phe Gln Asp Ile Tyr Pro Ser Ala Ala Val Gly Thr Tyr Asn Ser Gly
                    355                 360                 365

Ser Thr Thr Phe Asn Asp Ile Ile Ser Ala Val Gln Thr Tyr Gly Asp
                370                 375                 380

Gly Tyr Leu Ser Ile Val Glu Lys Tyr Thr Pro Ser Asp Gly Ser Leu
        385                 390                 395                 400

Thr Glu Gln Phe Ser Arg Thr Asp Gly Thr Pro Leu Ser Ala Ser Ala
                        405                 410                 415

Leu Thr Trp Ser Tyr Ala Ser Leu Leu Thr Ala Ser Ala Arg Arg Gln
                    420                 425                 430

Ser Val Val Pro Ala Ser Trp Gly Glu Ser Ala Ser Ser Val Leu
                    435                 440                 445

Ala Val Cys Ser Ala Thr Ser Ala Thr Gly Pro Tyr Ser Thr Ala Thr
                    450                 455                 460

Asn Thr Val Trp Pro Ser Ser Gly Ser Gly Ser Ser Thr Thr Thr Ser
        465                 470                 475                 480

Ser Ala Pro Cys Thr Thr Pro Thr Ser Val Ala Val Thr Phe Asp Glu
                        485                 490                 495
```

-continued

```
Ile Val Ser Thr Ser Tyr Gly Glu Thr Ile Tyr Leu Ala Gly Ser Ile
            500                 505                 510

Pro Glu Leu Gly Asn Trp Ser Thr Ala Ser Ala Ile Pro Leu Arg Ala
        515                 520                 525

Asp Ala Tyr Thr Asn Ser Asn Pro Leu Trp Tyr Val Thr Val Asn Leu
        530                 535                 540

Pro Pro Gly Thr Ser Phe Glu Tyr Lys Phe Phe Lys Asn Gln Thr Asp
545                 550                 555                 560

Gly Thr Ile Val Trp Glu Asp Pro Asn Arg Ser Tyr Thr Val Pro
                565                 570                 575

Ala Tyr Cys Gly Gln Thr Thr Ala Ile Leu Asp Asp Ser Trp Gln
            580                 585                 590
```

GLUCOAMYLASES AND METHODS OF USE, THEREOF

CROSS-REFERENCE TO RELATED APPLICATIONS

This application is a national stage entry under 35 U.S.C. § 371 of International Patent Application No. PCT/US2019/020876, filed Mar. 6, 2019, which claims priority to International Patent Application No. PCT/CN2018/078575, filed Mar. 9, 2018, the disclosure of each of which is incorporated by reference herein in its entirety.

FIELD OF THE INVENTION

The present disclosure relates to methods of saccharifying and/or hydrolyzing starch-containing materials using at least one glucoamylase. The glucoamylases of the present disclosure can also be used as a feed additive for animals to enhance starch digestion. Moreover, the disclosure also relates to methods of producing fermentation products as well as the fermentation products produced by the method thereof.

BACKGROUND

Glucoamylase (1,4-alpha-D-glucan glucohydrolase, EC 3.2.1.3) is an enzyme, which catalyzes the release of D-glucose from the non-reducing ends of starch or related oligo- and poly-saccharide molecules. Glucoamylases are produced by several filamentous fungi and yeast.

One non-limiting major application of glucoamylase is the saccharification of partially processed starch/dextrin to glucose, which is an essential substrate for numerous fermentation processes. The glucose may then be converted directly or indirectly into a fermentation product using a fermenting organism. Examples of commercial fermentation products include alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds.

Glucoamylase for commercial purposes has traditionally been produced employing filamentous fungi, although a diverse group of microorganisms is reported to produce glucoamylase, since they secrete large quantities of the enzyme extracellularly.

Saccharification or fermentation may be carried out at low pH, as typically fermentation organisms lower the pH rapidly, and some lactobacilli can further lower the pH to about 3.5. In another aspect, low pH values will minimize the risk of contamination. However, the commercially used fungal glucoamylases have certain limitations such as low pH sensitivity or low performance/activity at low pH (such as, for example, pH below 6).

Glucoamylases that are active at a low pH in the presence of pepsin can be useful as a feed additive for ruminants. Enzymes for use as feed additives for ruminants are mainly fibrolytic enzymes, such as cellulases, beta-glucanases and hemicellulases (Table 1 in Beauchemin et al., 2004). A rationale for the development of feed enzyme products for ruminants. *Can. J. Anim. Sci.* 84: 23-36). Reports on starch hydrolases for ruminant uses are limited.

The digestibility of starch in feeds and feed sources is highly variable and dependent on a number of factors including the physical structure of both the starch and feed matrix. US Patent Application Publication 2005/0037053, published on Feb. 17, 2005, discloses the use of an enzyme having amylase activity and capable of degrading resistant starch in a feed comprising starch for monogastric animals such as poultry and swine. WO 2008/06881, published on Jan. 17, 2008, discloses the use of bacterial amylases in feed for ruminant animals of the subfamily Bovinae for improving milk yield, apparent digestibility of the diet fed, feedstuff dry matter disappearance, weight gain and/or Feed Conversion Ratio. WO 2015/128366, published on Sep. 3, 2015, discloses the use of bacterial amylases in combination with one or more proteases in feed for ruminant animals of the subfamily Bovinae for improving digestibility of maize and/or maize silages, in particular for improving milk yield, weight gain and/or Feed Conversion Ratio. Accordingly, there is still a need to increase starch digestibility for animals.

Accordingly, there is a need to search for new glucoamylases to improve low pH tolerance during saccharification and/or fermentation or to increase starch digestibility for an animal fed a starch-containing diet.

SUMMARY

The present disclosure relates to methods of saccharifying starch-containing materials using at least one glucoamylase. The glucoamylases of the present disclosure can also be used as a feed additive for animals to enhance starch digestion. Aspects and embodiments of the methods are described in the following, independently-numbered paragraphs.

1. In one aspect, a method for saccharifying a starch substrate, comprising contacting the starch substrate with a glucoamylase selected from the group consisting of:
   a) a polypeptide having the amino acid sequence of SEQ ID NO: 7, or 8 or 9;
   b) a polypeptide having at least 83% identity to the amino acid sequence of SEQ ID NO: 7 or 8;
   c) a polypeptide having at least 83% identity to a catalytic domain of SEQ ID NO: 7, or 8;
   d) a polypeptide having the amino acid sequence of the catalytic domain of SEQ ID NO: 9; or
   e) a mature polypeptide produced by the processing of the polypeptide of SEQ ID NO: 1, 2, or 3 by a signal peptidase or post translational modification during secretion from an expression host;
   wherein the saccharifying is carried out at a pH between 2.0 and 6.0,
2. In some embodiments of the method of paragraph 1, wherein saccharifying the starch substrate results in a high glucose syrup.
3. In some embodiments of the method of paragraph 1 or 2, wherein the high glucose syrup comprises an amount of glucose selected from the list consisting of at least 95.5% glucose.
4. In some embodiments of the method of any one of paragraphs 1-3, further comprising fermenting the high glucose syrup to an end product.
5. In some embodiments of the method of paragraph 4, wherein saccharifying and fermenting are carried out as a simultaneous saccharification and fermentation (SSF) process.
6. In some embodiments of the method of paragraph 4 or 5, wherein the end product is alcohol, for example, ethanol.
7. In some embodiments of the method of paragraph 4 or 5, wherein the end product is a biochemical selected from the group consisting of an amino acid, an organic acid, citric acid, lactic acid, succinic acid, monosodium glutamate, gluconic acid, sodium gluconate, calcium gluconate, potassium gluconate, glucono delta-lactone, sodium erythorbate, omega 3 fatty acid, butanol, lysine, itaconic acid, 1,3-propanediol, biodiesel, and isoprene.

8. In some embodiments of the method of any one of paragraphs 1-7, wherein the starch substrate is about, 5% to 99%, 15% to 50% or 40-99% dry solid (DS).

9. In some embodiments of the method of any one of paragraphs 1-8, wherein the starch substrate is selected from wheat, barley, corn, rye, rice, sorghum, bran, cassava, milo, millet, potato, sweet potato, tapioca, and any combination thereof.

10. In some embodiments of the method of any one of paragraphs 1-9, wherein the starch substrate comprises liquefied starch, gelatinized starch, or granular starch.

11. In some embodiments of the method of any one of paragraphs 1-10, further comprising adding a hexokinase, a xylanase, a glucose isomerase, a xylose isomerase, a phosphatase, a phytase, a pullulanase, a beta-amylase, an alpha-amylase, a glucoamylase, a protease, a cellulase, a hemicellulase, a lipase, a cutinase, a trehalase, an isoamylase, a redox enzyme, an esterase, a transferase, a pectinase, a hydrolase, an alpha-glucosidase, a beta-glucosidase, or a combination thereof to the starch substrate.

12. In another aspect, a method for saccharifying and fermenting a starch substrate to produce an end product, comprising contacting the starch substrate with a glucoamylase selected from the group consisting of:
  a) a polypeptide having the amino acid sequence of SEQ ID NO: 7, or 8 or 9;
  b) a polypeptide having at least 83% identity to the amino acid sequence of SEQ ID NO: 7 or 8;
  c) a polypeptide having at least 83% identity to a catalytic domain of SEQ ID NO: 7, or 8;
  d) a polypeptide having the amino acid sequence of the catalytic domain of SEQ ID NO: 9; or
  e) a mature polypeptide produced by the processing of the polypeptide of SEQ ID NO: 1, 2, or 3 by a signal peptidase or post translational modification during secretion from an expression host;
  wherein the saccharifying and fermenting is carried out at a pH between 2.0 and 6.0, preferably between pH 2.0 and pH 5.0, preferably between pH 2.0 and pH 4.0, more preferably between pH 2.0 and pH 3.0.

13. In some embodiments of the method of paragraph 12, wherein saccharifying and fermenting are carried out as a simultaneous saccharification and fermentation (SSF) process.

14. In some embodiments of the method of paragraph 12 or 13, wherein the end product is alcohol, for example, ethanol.

15. In some embodiments of the method of paragraph 12, wherein the saccharified and fermented starch substrate results in a reduced level of DP3+ and an increased level of DP1 compared to contacting the same starch substrate with AnGA.

16. In some embodiments of the method of paragraph 12 or 13, wherein the end product is a biochemical selected from the group consisting of an amino acid, an organic acid, citric acid, lactic acid, succinic acid, monosodium glutamate, gluconic acid, sodium gluconate, calcium gluconate, potassium gluconate, glucono delta-lactone, sodium erythorbate, omega 3 fatty acid, butanol, lysine, itaconic acid, 1,3-propanediol, biodiesel, and isoprene.

17. In another aspect, a method for increasing starch digestibility in an animal which comprises adding at least one glucoamylase selected from the group consisting of:
  a) a polypeptide having the amino acid sequence of SEQ ID NO: 7, or 8 or 9;
  b) a polypeptide having at least 83% identity to the amino acid sequence of SEQ ID NO: 7 or 8;
  c) a polypeptide having at least 83% identity to a catalytic domain of SEQ ID NO: 7, or 8;
  d) a polypeptide having the amino acid sequence of the catalytic domain of SEQ ID NO: 9; or
  e) a mature polypeptide produced by the processing of the polypeptide of SEQ ID NO: 1, 2, or 3 by a signal peptidase or post translational modification during secretion from an expression host;
  as a feed additive to feed for an animal wherein said glucoamylase (a) has at least 20% activity or at least 20% greater residual activity at pH less than or equal to 3 in the presence of pepsin or rumin fluid (e.g., pepsin-containing rumen fluid) as compared to activity of the enzymes at pH 6 alone or in the presence of or rumin fluid (e.g., pepsin-containing rumen fluid), and (b) the enzyme works with pancreatic amylase to increase glucose yield.

18. In some embodiments of the method of paragraph 17, wherein when the animal is a ruminant said enzyme is active in at least two of three digestive chambers of the ruminant comprising a rumen, an abomasum and a small intestine 19. In some embodiments of the method of paragraph 16 or 17, wherein said at least one glucoamylase is capable of hydrolyzing raw starch.

20. In another aspect, a polynucleotide comprising a nucleotide sequence that has at least 80% identity to the nucleotide sequence of SEQ ID NO: 4, 5 or 6.

21. In another aspect, a vector comprising the polynucleotide sequence of paragraph 20 operably linked to one or more control sequences that control the production of the encoded polypeptide in an expression host, and wherein said regulatory sequence is heterologous to the coding nucleotide sequence, or said regulatory sequence and coding sequence are not arranged as found together in nature.

22. In another aspect, a recombinant host cell comprising the polynucleotides of paragraph 20.

23. In some embodiments of the recombinant host cell of paragraph 22, which is a *Trichoderma, Aspergillus*, Myceliopthora or *Saccharomyces* cell.

24. In some embodiments of the recombinant host cell of paragraph 22, which is an *E. coli, Bacillus, Streptomyces*, or *Pseudomonas* cell.

25. In some embodiments of the recombinant host cell of paragraph 22, which is an ethanologenic microorganisms.

26. In some embodiments of the recombinant host cell of any one of paragraphs 22-25, which further expresses and secretes one or more additional enzymes selected from the group comprising protease, hemicellulase, cellulase, peroxidase, lipolytic enzyme, metallolipolytic enzyme, xylanase, lipase, phospholipase, esterase, perhydrolase, cutinase, pectinase, pectate lyase, mannanase, keratinase, reductase, oxidase, phenoloxidase, lipoxygenase, ligninase, alpha-amylase, pullulanase, phytase, tannase, pentosanase, malanase, beta-glucanase, arabinosidase, hyaluronidase, chondroitinase, laccase, transferrase, or a combination thereof.

27. In another aspect, a feed additive composition or premix comprising at least one glucoamylase selected from the group consisting of:
  (a) a polypeptide having the amino acid sequence of SEQ ID NO: 7, 8, or 9;
  (b) a polypeptide having at least 83% identity to the amino acid sequence of SEQ ID NO: 7, 8, or 9;

(c) a polypeptide having at least 83% identity to a catalytic domain of SEQ ID NO: 7, 8, or 9;

(d) a polypeptide having at least 83% identity to a linker and a catalytic domain of SEQ ID NO: 7, 8, or 9; or (e) a mature polypeptide produced by the processing of the polypeptide of SEQ ID NO: 1, 2, or 3 by a signal peptidase or post translational modification during secretion from an expression host; and/or (f) optionally at least one mineral and/or at least one vitamin.

28. In some embodiments of the feed additive composition or premix of paragraph 27, which further comprises one or more of the enzymes selected from the group consisting of a protease, an amylase, a xylanase, and a phytase.

29. In some embodiments of the feed additive composition or premix of paragraph 27 or paragraph 28, which further comprises one or more direct fed microbial selected from the group consisting of *Bacillus*, Lactic Acid Bacteria and Yeasts.

BRIEF DESCRIPTION OF THE DRAWINGS AND SEQUENCES

FIG. 1 is a CLUSTALW multiple sequence alignment of TeGA, FraGA1, WcoGA1 and other fungal glucoamylases.

The following sequences comply with 37 C.F.R. §§ 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. § 1.822.

SEQ ID NO: 1 is precursor protein sequence of the FraGA1.

SEQ ID NO: 2 is precursor protein sequence of the WcoGA1.

SEQ ID NO: 3 is precursor protein sequence of the TeGA.

SEQ ID NO: 4 is nucleotide sequence of the FraGA1 gene.

SEQ ID NO: 5 is nucleotide sequence of the WcoGA1 gene.

SEQ ID NO: 6 is nucleotide sequence of the TeGA gene.

SEQ ID NO: 7 is predicted mature protein sequence of the FraGA1.

SEQ ID NO: 8 is predicted mature protein sequence of the WcoGA1.

SEQ ID NO: 9 is mature protein sequence of the TeGA.

SEQ ID NO: 10 is wild type glucoamylase from *Aspergillus niger*, and the NCBI accession number is XP_001390530.1.

SEQ ID NO: 11 is wild type glucoamylase from *Trichoderma reesei*, and the PDB accession number is 2VN4_A.

SEQ ID NO: 12 is KZT67263.1 (NCBI accession number).

SEQ ID NO: 13 is XP_002475369.1 (NCBI accession number).

SEQ ID NO: 14 is SEQ ID NO: 1847 described in US20090325240.

SEQ ID NO: 15 is KZT09226.1 (NCBI accession number).

SEQ ID NO: 16 is SEQ ID NO: 12 described in WO2016196202.

SEQ ID NO: 17 is SEQ ID NO: 2 described in US20170314003.

SEQ ID NO: 18 is GAD95639.1 (NCBI accession number).

SEQ ID NO: 19 is SEQ ID NO: 23 described in US20170306309.

SEQ ID NO:20 is CAC28076.1 (NCBI accession number).

DETAILED DESCRIPTION

All patents, patent applications, and publications cited are incorporated herein by reference in their entirety. In this disclosure, a number of terms and abbreviations are used. The following definitions apply unless specifically stated otherwise.

The term "comprising" means the presence of the stated features, integers, steps, or components as referred to in the claims, but that it does not preclude the presence or addition of one or more other features, integers, steps, components or groups thereof. The term "comprising" is intended to include embodiments encompassed by the terms "consisting essentially of" and "consisting of". Similarly, the term "consisting essentially of" is intended to include embodiments encompassed by the term "consisting of". As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

Unless otherwise defined, all technical and scientific terms used have their ordinary meaning in the relevant scientific field. Singleton, et al., Dictionary of Microbiology and Molecular Biology, 2d Ed., John Wiley and Sons, New York (1994), and Hale & Markham, Harper Collins Dictionary of Biology, Harper Perennial, NY (1991) provide the ordinary meaning of many of the terms describing the invention.

The term "glucoamylase (1,4-alpha-D-glucan glucohydrolase, EC 3.2.1.3) activity" is defined herein as an enzyme activity, which catalyzes the release of D-glucose from the non-reducing ends of starch or related oligo- and polysaccharide molecules. The majority of glucoamylases are multidomain enzymes consisting of a catalytic domain connected to a starch binding domain by an O-glycosylated linker region of varying lengths. The crystal structures of multiple glucoamylases have been determined and described (see J. Lee and M. Paetzel 2011. Acta Cryst. Vol. 67 pages 188-192 "Structure of the catalytic domain of glucoamylase from *Aspergillus niger*" and J. Sauer et al 2000. Biochem. Et Biophys. Acta Vol. 1542 page 275-293 "Glucoamylase: structure/function relationships, and protein engineering".

The terms "starch binding domain (SBD) or carbohydrate binding module (CBM)" are used interchangeably herein. SBDs can be divided into nine CBM families. As a source of energy, starch is degraded by a large number of various amylolytic enzymes. However, only about 10% of them are capable of binding and degrading raw starch. These enzymes usually possess a distinct sequence-structural module called the starch-binding domain that mediates attachment to starch granules. SBD refers to an amino acid sequence that binds preferentially to a starch (polysaccharide) substrate or a maltosaccharide, alpha-, beta and gamma-cyclodextrin and the like. They are usually motifs of approximately 100 amino acid residues found in about 10% of microbial amylolytic enzymes.

The term "catalytic domain (CD)" refers to a structural region of a polypeptide which contains the active site for substrate hydrolysis.

The term "glycoside hydrolase" is used interchangeably with "glycosidases" and "glycosyl hydrolases". Glycoside hydrolases assist in the hydrolysis of glycosidic bonds in complex sugars (polysaccharides, such as, without limitation, starch). Glycoside hydrolases can also be classified as exo- or endo-acting, dependent upon whether they act at the (usually non-reducing) end or in the middle, respectively, of an oligo/polysaccharide chain. Glycoside hydrolases may also be classified by sequence or structure based methods.

The term "feed" is used with reference to products that are fed to animals in the rearing of livestock. The terms "feed" and "animal feed" are used interchangeably. In a preferred embodiment, the food or feed is for consumption by non-ruminants and ruminants.

The term "direct fed microbial" ("DFM") as used herein is source of live (viable) naturally occurring microorganisms. Categories of DFMs include *Bacillus*, Lactic Acid Bacteria and Yeasts. *Bacillus* are unique, gram-positive rods that form spores. Types of Lactic Acid Bacteria include *Bifidobacterium, Lactobacillus* and *Streptococcus*. Yeasts are not bacteria. These microorganisms belong to the plant group fungi.

The term "pepsin" as used herein refers to an enzyme that breaks down proteins into smaller peptides at a low pH from 2.0 to 3.5, i.e., it is a protease belonging to Aspartic peptidase family A1. It is produced and secreted into the stomach and is one of the main digestive enzymes in the digestive systems of humans and animals, where it helps digesting the proteins in food or feed.

The term "ruminant" as used herein refers to a mammal that is able to acquire nutrients from plant-based food by fermenting it in a specialized stomach prior to digestion, principally, through microbial actions.

The term "digestive chambers of a ruminant" as used herein refer to the rumen, reticulum, omasum, abomasum and small intestine (McDonald et al., 2011, Animal Nutrition (7th Edition), pages 156-191). The abomasum is the direct equivalent of the monogastric stomach.

The term "granular starch" refers to raw (uncooked) starch, e.g., granular starch that has not been subject to gelatinization.

The terms "granular starch hydrolyzing (GSH) enzyme" and "granular starch hydrolyzing (GSH) activity" are used interchangeably herein and refer to enzymes, which have the ability to hydrolyze starch in granular form under digestive tract relevant conditions comparable to the conditions found in the digestive tract of animals and, in particular, ruminants.

The term "isolated" means a substance in a form or environment that does not occur in nature. Non-limiting examples of isolated substances include (1) any non-naturally occurring substance, (2) any substance including, but not limited to, any host cell, enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated. The terms "isolated nucleic acid molecule", "isolated polynucleotide", and "isolated nucleic acid fragment" will be used interchangeably and refer to a polymer of RNA or DNA that is single- or double-stranded, optionally containing synthetic, non-natural or altered nucleotide bases.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified."

The terms "peptides", "proteins" and "polypeptides" are used interchangeably herein and refer to a polymer of amino acids joined together by peptide bonds. A "protein" or "polypeptide" comprises a polymeric sequence of amino acid residues. The single and 3-letter code for amino acids as defined in conformity with the IUPAC-IUB Joint Commission on Biochemical Nomenclature (JCBN) is used throughout this disclosure. It is also understood that a polypeptide may be coded for by more than one nucleotide sequence due to the degeneracy of the genetic code.

The term "mature" form of a protein, polypeptide, or enzyme refers to the functional form of the protein, polypeptide, or enzyme without a signal peptide sequence or a propeptide sequence.

The term "precursor" form of a protein or peptide refers to a form of the protein having a prosequence operably linked to the amino or carbonyl terminus of the protein. The precursor may also have a "signal" sequence operably linked to the amino terminus of the prosequence.

As noted above, regulatory sequences can be operably linked in sense or antisense orientation to the coding sequence/gene of interest.

"Promoter" or "promoter sequences" refer to DNA sequences that define where transcription of a gene by RNA polymerase begins. Promoter sequences are typically located directly upstream or at the 5' end of the transcription initiation site. Promoters may be derived in their entirety from a native or naturally occurring sequence, or be composed of different elements derived from different promoters found in nature, or even comprise synthetic DNA segments. It is understood by those skilled in the art that different promoters may direct the expression of a gene in different tissues or cell type or at different stages of development, or in response to different environmental or physiological conditions ("inducible promoters").

The "3' non-coding sequences" refer to DNA sequences located downstream of a coding sequence and include sequences encoding regulatory signals capable of affecting mRNA processing or gene expression, such as termination of transcription.

The term "transformation" as used herein refers to the transfer or introduction of a nucleic acid molecule into a host organism. The nucleic acid molecule may be introduced as a linear or circular form of DNA. The nucleic acid molecule may be a plasmid that replicates autonomously, or it may integrate into the genome of a production host. Production hosts containing the transformed nucleic acid are referred to as "transformed" or "recombinant" or "transgenic" organisms or "transformants".

The term "recombinant" as used herein refers to an artificial combination of two otherwise separated segments of nucleic acid sequences, e.g., by chemical synthesis or by the manipulation of isolated segments of nucleic acids by genetic engineering techniques. For example, DNA in which one or more segments or genes have been inserted, either naturally or by laboratory manipulation, from a different molecule, from another part of the same molecule, or an artificial sequence, resulting in the introduction of a new sequence in a gene and subsequently in an organism. The terms "recombinant", "transgenic", "transformed", "engineered" or "modified for exogenous gene expression" are used interchangeably herein.

The terms "recombinant construct", "expression construct", "recombinant expression construct" and "expression cassette" are used interchangeably herein. A recombinant construct comprises an artificial combination of nucleic acid fragments, e.g., regulatory and coding sequences that are not all found together in nature. For example, a construct may comprise regulatory sequences and coding sequences that are derived from different sources, or regulatory sequences and coding sequences derived from the same source, but arranged in a manner different than that found in nature. Such a construct may be used by itself or may be used in conjunction with a vector.

The term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the number of matching nucleotides or amino acids between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, N Y (1993); *Computer Analysis of Sequence Data, Part I* (Griffin, A. M., and Griffin, H. G., eds.) Humana Press, N J (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs.

As used herein, "% identity" or percent identity" or "PID" refers to protein sequence identity. Percent identity may be determined using standard techniques known in the art. Useful algorithms include the BLAST algorithms (See, Altschul et al., J Mol Biol, 215:403-410, 1990; and Karlin and Altschul, Proc Natl Acad Sci USA, 90:5873-5787, 1993). The BLAST program uses several search parameters, most of which are set to the default values. The NCBI BLAST algorithm finds the most relevant sequences in terms of biological similarity but is not recommended for query sequences of less than 20 residues (Altschul et al., Nucleic Acids Res, 25:3389-3402, 1997; and Schaffer et al., Nucleic Acids Res, 29:2994-3005, 2001). Exemplary default BLAST parameters for a nucleic acid sequence searches include: Neighboring words threshold=11; E-value cut-off=10; Scoring Matrix=NUC.3.1 (match=1, mismatch=−3); Gap Opening=5; and Gap Extension=2. Exemplary default BLAST parameters for amino acid sequence searches include: Word size=3; E-value cutoff=10; Scoring Matrix=BLOSUM62; Gap Opening=11; and Gap extension=1. A percent (%) amino acid sequence identity value is determined by the number of matching identical residues divided by the total number of residues of the "reference" sequence including any gaps created by the program for optimal/maximum alignment. BLAST algorithms refer to the "reference" sequence as the "query" sequence.

As used herein, "homologous proteins" or "homologous enzymes" refers to proteins that have distinct similarity in primary, secondary, and/or tertiary structure. Protein homology can refer to the similarity in linear amino acid sequence when proteins are aligned. Homologous search of protein sequences can be done using BLASTP and PSI-BLAST from NCBI BLAST with threshold (E-value cut-off) at 0.001. (Altschul S F, Madde T L, Shaffer A A, Zhang J, Zhang Z, Miller W, Lipman D J. Gapped BLAST and PSI BLAST a new generation of protein database search programs. Nucleic Acids Res 1997 Set 1; 25(17):3389-402). Using this information, proteins sequences can be grouped, and a phylogenetic tree can also be built using the amino acid sequences. Sequence alignments and percent identity calculations may also be performed using the Megalign program, the AlignX program, the EMBOSS Open Software Suite (EMBL-EBI; Rice et al., *Trends in Genetics* 16, (6):276-277 (2000)) or similar programs. Multiple alignment of the sequences can also be performed using the CLUSTAL method (such as CLUSTALW) with the default parameters. Suitable parameters for CLUSTALW protein alignments include GAP Existence penalty=15, GAP extension=0.2, matrix=Gonnet (e.g., Gonnet250), protein END-GAP=−1, protein GAPDIST=4, and KTUPLE=1.

Various polypeptide amino acid sequences and polynucleotide sequences are disclosed herein as features of certain aspects. Variants of these sequences that are at least about 70-85%, 85-90%, or 90%-95% identical to the sequences disclosed herein may be used in certain embodiments. Alternatively, a variant polypeptide sequence or polynucleotide sequence in certain embodiments can have at least 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function of the disclosed sequences, or at least about 85%, 86%, 87%, 88%, 89%, 90%, 91%, 92%, 93%, 94%, 95%, 96%, 97%, 98%, or 99% of the function of the disclosed sequences.

In one aspect, the mature polypeptide is amino acids 17 to 567 of SEQ ID NO: 1, 18 to 569 of SEQ ID NO: 2 and 28 to 618 of SEQ ID NO: 3 based on the SignalP (Nielsen et al., 1997, *Protein Engineering* 10: 1-6) program.

The term "nucleic acid" encompasses DNA, RNA, heteroduplexes, and synthetic molecules capable of encoding a polypeptide. Nucleic acids may be single stranded or double stranded, and may be chemically modified. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. Unless otherwise indicated, nucleic acid sequences are presented in 5'-to-3' orientation.

The term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

A "synthetic" molecule is produced by in vitro chemical or enzymatic synthesis rather than by an organism.

A "host strain" or "host cell" is an organism into which an expression vector, phage, virus, or other DNA construct, including a polynucleotide encoding a polypeptide of interest (e.g., an amylase) has been introduced. Exemplary host strains are microorganism cells (e.g., bacteria, filamentous fungi, and yeast) capable of expressing the polypeptide of interest and/or fermenting saccharides. The term "host cell" includes protoplasts created from cells.

The term "expression" refers to the process by which a polypeptide is produced based on a nucleic acid sequence. The process includes both transcription and translation.

The term "end product" refers to an alcohol such as ethanol, or a biochemical selected from the group consisting of an amino acid, an organic acid, citric acid, lactic acid, succinic acid, monosodium glutamate, gluconic acid, sodium gluconate, calcium gluconate, potassium gluconate, glucono delta-lactone, sodium erythorbate, omega 3 fatty acid, butanol, lysine, itaconic acid, 1,3-propanediol, biodiesel, and isoprene The term "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a DNA construct comprising a DNA sequence encoding a polypeptide of interest, which coding sequence is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

A "signal sequence" is a sequence of amino acids attached to the N-terminal portion of a protein, which facilitates the secretion of the protein outside the cell. The mature form of an extracellular protein lacks the signal sequence, which is cleaved off during the secretion process.

"Biologically active" refer to a sequence having a specified biological activity, such an enzymatic activity.

The term "specific activity" refers to the number of moles of substrate that can be converted to product by an enzyme or enzyme preparation per unit time under specific conditions. Specific activity is generally expressed as units (U)/mg of protein.

As used herein, the term "residual activity" refers to the ratio of activities with respect to a substrate measured with and without incubation at a specific condition (such as, without limitation, altered temperature or altered pH).

The terms, "wild-type," "parental," or "reference," with respect to a polypeptide, refer to a naturally-occurring polypeptide that does not include a man-made substitution, insertion, or deletion at one or more amino acid positions.

Similarly, the terms "wild-type," "parental," or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

The terms "thermally stable", "thermostable" and "thermostability," with reference to an enzyme, refer to the ability of the enzyme to retain activity after exposure to an elevated temperature. The thermostability of an enzyme, such as an amylase enzyme, is measured by its half-life ($t_{1/2}$) given in minutes, hours, or days, during which half the enzyme activity is lost under defined conditions. The half-life may be calculated by measuring residual amylase activity for example following exposure to (i.e., challenge by) an elevated temperature. The terms "thermally stable" and "thermostable" mean that at least about 50%, 55%, 60%, 65%, 70%, 75%, 80%, 85%, 90%, 95%, 96%, 97% or 98% of the enzyme that was present/active in the additive before heating to the specified temperature is still present/active after it cools to room temperature. Preferably, at least about 80% of the enzyme that is present and active in the additive before heating to the specified temperature is still present and active after it cools to room temperature.

A "pH range," with reference to an enzyme, refers to the range of pH values under which the enzyme exhibits catalytic activity.

The terms "pH stable" and "pH stability," with reference to an enzyme, relate to the ability of the enzyme to retain activity over a wide range of pH values for a predetermined period of time (e.g., 15 min., 30 min., 1 hour).

The phrase "simultaneous saccharification and fermentation (SSF)" refers to a process in the production of biochemicals in which a microbial organism, such as an ethanologenic microorganism, and at least one enzyme, such as an amylase, are present during the same process step. SSF includes the contemporaneous hydrolysis of starch substrates (granular, liquefied, or solubilized) to saccharides, including glucose, and the fermentation of the saccharides into alcohol or other biochemical or biomaterial in the same reactor vessel.

A "slurry" is an aqueous mixture containing insoluble starch granules in water.

The term "total sugar content" refers to the total soluble sugar content present in a starch composition including monosaccharides, oligosaccharides and polysaccharides.

The term "dry solids" (ds) refer to dry solids dissolved in water, dry solids dispersed in water or a combination of both. Dry solids thus include granular starch, and its hydrolysis products, including glucose.

"Dry solid content" refers to the percentage of dry solids both dissolved and dispersed as a percentage by weight with respect to the water in which the dry solids are dispersed and/or dissolved. The initial dry solid content of starch is the weight of granular starch corrected for moisture content over the weight of granular starch plus weight of water. Subsequent dry solid content can be determined from the initial content adjusted for any water added or lost and for chemical gain. Subsequent dissolved dry solid content can be measured from refractive index as indicated below. 8

The term "high DS" refers to aqueous starch slurry with a dry solid content greater than 38% (wt/wt).

"Dry substance starch" refers to the dry starch content of a substrate, such as a starch slurry, and can be determined by subtracting from the mass of the substrate any contribution of non-starch components such as protein, fiber, and water. For example, if a granular starch slurry has a water content of 20% (wt/wt), and a protein content of 1% (wt/wt), then 100 kg of granular starch has a dry starch content of 79 kg. Dry substance starch can be used in determining how many units of enzymes to use.

"Liquefact" refers to the product of cooking (heating) and liquefaction (reduction of viscosity) of a starch or starch containing grain slurry (mash).

"Liquefaction" or "liquefy" refers to a process by which starch (or starch containing grains) is/are converted to shorter chain and less viscous dextrins.

"Degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. A DP4+(>DP3) denotes polymers with a degree of polymerization of greater than 3.

The term "contacting" refers to the placing of referenced components (including but not limited to enzymes, substrates, and fermenting organisms) in sufficiently close proximity to affect an expect result, such as the enzyme acting on the substrate or the fermenting organism fermenting a substrate. Those skilled in the art will recognize that mixing solutions can bring about "contacting."

An "ethanologenic microorganism" refers to a microorganism with the ability to convert a sugar or other carbohydrates to ethanol.

The term "biochemicals" refers to a metabolite of a microorganism, such as citric acid, lactic acid, succinic acid, monosodium glutamate, gluconic acid, sodium gluconate, calcium gluconate, potassium gluconate, glucono delta-lactone, sodium erythorbate, omega 3 fatty acid, butanol, iso-butanol, an amino acid, lysine, itaconic acid, other organic acids, 1,3-propanediol, vitamins, or isoprene or other biomaterial.

The term "about" refers to ±15% to the referenced value.

The following abbreviations/acronyms have the following meanings unless otherwise specified:
EC enzyme commission
CAZy carbohydrate active enzyme
w/v weight/volume
w/w weight/weight
v/v volume/volume
wt % weight percent
° C. degrees Centigrade
g or gm gram
µg microgram
mg milligram
kg kilogram
µL and µl microliter
mL and ml milliliter
mm millimeter
µm micrometer
mol mole
mmol millimole
M molar
mM millimolar
µM micromolar
nm nanometer
U unit
ppm parts per million
hr and h hour In a first aspect, the present invention relates to polypeptides comprising an amino acid sequence having preferably at least 83%, at least 85%, at least 90%, at least 92%, at least 93%, at least 94%, at least 95%, at least 96%, at least 97%, at least 98%, and even at least 99%, amino acid sequence identity to the polypeptide of SEQ ID NO: 7, 8 or 9, and having glucoamylase activity.

In some embodiments, the polypeptides of the present invention are the homologous polypeptides comprising amino acid sequences differ by ten amino acids, preferably by nine amino acids, preferably by eight amino acids, preferably by seven amino acids, preferably by six amino acids, preferably by five amino acids, more preferably by four amino acids, even more preferably by three amino acids, most preferably by two amino acids, and even most preferably by one amino acid from the polypeptide of SEQ ID N07, 8 or 9.

In some embodiments, the polypeptides of the present invention are the variants of polypeptide of SEQ ID NO: 7, 8 or 9, or a fragment thereof having glucoamylase activity.

In some embodiments, the polypeptides of the present invention are the catalytic regions comprising the amino acids 17-470 of SEQ ID NO: 1, 18-472 of SEQ ID NO: 2 or 28-500 of SEQ ID NO: 3 predicted by ClustalX https://www.ncbi.nlm.nih.gov/pubmed/17846036.

In some embodiments, the polypeptides of the present invention are low pH stable and retain glucoamylase activity at low pH. The polypeptides of the present invention have shown low pH stability at pH values ranging from about 2.0 to about 5.0 (e.g., about 2.0 to about 4.0, about 2.0 to about 3.0, about 2.0 to about 2.5, etc). For example, at pH 2.0 to about 3.0, the polypeptides of the present invention retain most of glucogenic activity for an extended period of time at high temperature (e.g. at least 40° C., at least 50° C., at least 55° C., at least 60° C., at least 65° C., at least 70° C. or a higher temperature), and for example, for at least 4 hours, at least 17 hours, at least 24 hours, at least 48 hours, at least 72 hours, or even longer.

In some embodiments, the polypeptides of the present invention have better saccharification performance in comparison with (a glucoamylase from *Aspergillus niger*) AnGA, at a pH of about 3, or even at a pH of about 2, at a temperature range from about 30 to about 70° C., (e.g., about 30° C. to about 60° C., about 40° C. to about 60° C., etc.) with incubation time for at least 24 hours, at least 48 hours, at least 72 hours, or even longer.

In some embodiments, the polypeptides of the present invention can be used in simultaneous saccharification and fermentation (SSF) process or low pH fermentation in comparison with the current commercial available glucoamylase products, at a pH of about 3, or even at a pH of about 2, at a temperature range from about 30° C. to about 70° C., (e.g., about 30° C. to about 60° C., about 30° C. to about 50° C., etc.) with incubation time for at least 17 hours, at least 24 hours, at least 48 hours, at least 72 hours, or even longer.

In a second aspect, the present glucoamylases comprise conservative substitution of one or several amino acid residues relative to the amino acid sequence of SEQ ID NO: 7, 8, or 9. Exemplary conservative amino acid substitutions are listed in the Table 1. Some conservative mutations can be produced by genetic manipulation, while others are produced by introducing synthetic amino acids into a polypeptide by other means.

TABLE 1

Conservative amino acid substitutions

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

In some embodiments, the present glucoamylase comprises a deletion, substitution, insertion, or addition of one or a few amino acid residues relative to the amino acid sequence of SEQ ID NO: 7, 8, or 9 or a homologous sequence thereof. In some embodiments, the present glucoamylases are derived from the amino acid sequence of SEQ ID NO: 7, 8, or 9 by conservative substitution of one or several amino acid residues. In some embodiments, the present glucoamylases are derived from the amino acid sequence of SEQ ID N07, 8, or 9 by deletion, substitution, insertion, or addition of one or a few amino acid residues relative to the amino acid sequence of SEQ ID NO: 7, 8, or 9. In all cases, the expression "one or a few amino acid residues" refers to 10 or less, i.e., 1, 2, 3, 4, 5, 6, 7, 8, 9, or 10, amino acid residues. The amino acid substitutions, deletions and/or insertions of the mature polypeptide of SEQ ID NO: 7, 8, or 9 can be at most 10, preferably at most 9, more preferably at most 8, more preferably at most 7, more preferably at most 6, more preferably at most 5, more preferably at most 4, even more preferably at most 3, most preferably at most 2, and even most preferably at most 1.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochem. 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The glucoamylase may be a "chimeric" or "hybrid" polypeptide, in that it includes at least a portion from a first glucoamylase, and at least a portion from a second amylase, glucoamylase, beta-amylase, alpha-glucosidase or other starch degrading enzymes, or even other glycosyl hydrolases, such as, without limitation, cellulases, hemicellulases, etc. (including such chimeric amylases that have recently been "rediscovered" as domain-swap amylases). The present glucoamylases may further include heterologous signal sequence, an epitope to allow tracking or purification, or the like.

The present glucoamylases can be produced in host cells, for example, by secretion or intracellular expression. A cultured cell material (e.g., a whole-cell broth) comprising a glucoamylase can be obtained following secretion of the glucoamylase into the cell medium. Optionally, the glucoamylase can be isolated from the host cells, or even isolated from the cell broth, depending on the desired purity of the final glucoamylase. A gene encoding a glucoamylase can be cloned and expressed according to methods well known in the art. Suitable host cells include bacterial, fungal (including yeast and filamentous fungi), and plant cells (including algae). Particularly useful host cells include *Aspergillus niger, Aspergillus oryzae, Trichoderma reesi* or *Myceliopthora thermophila*. Other host cells include bacterial cells, e.g., *Bacillus subtilis* or *B. licheniformis*, as well as *Streptomyces*.

Additionally, the host may express one or more accessory enzymes, proteins, peptides. These may benefit liquefaction, saccharification, fermentation, SSF, and downstream processes. Furthermore, the host cell may produce ethanol and other biochemicals or biomaterials in addition to enzymes used to digest the various feedstock(s). Such host cells may be useful for fermentation or simultaneous saccharification and fermentation processes to reduce or eliminate the need to add enzymes.

A DNA construct comprising a nucleic acid encoding a glucoamylase polypeptide can be constructed such that it is suitable to be expressed in a host cell. Because of the known degeneracy in the genetic code, different polynucleotides that encode an identical amino acid sequence can be designed and made with routine skill. It is also known that, depending on the desired host cells, codon optimization may be required prior to attempting expression.

A polynucleotide encoding a glucoamylase polypeptide of the present disclosure can be incorporated into a vector. Vectors can be transferred to a host cell using known transformation techniques, such as those disclosed below.

A suitable vector may be one that can be transformed into and replicated within a host cell. For example, a vector comprising a nucleic acid encoding a glucoamylase polypeptide of the present disclosure can be transformed and replicated in a bacterial host cell as a means of propagating and amplifying the vector. The vector may also be suitably transformed into an expression host, such that the encoding polynucleotide is expressed as a functional glucoamylase enzyme.

A polynucleotide encoding a glucoamylase polypeptide of the present invention can be operably linked to a promoter, which allows transcription in the host cell. The promoter may be any DNA sequence that shows transcriptional activity in the host cell of choice and may be derived from genes encoding proteins either homologous or heterologous to the host cell.

The coding sequence can be operably linked to a signal sequence. The DNA encoding the signal sequence may be a DNA sequence naturally associated with the glucoamylase gene of interest to be expressed, or may be from a different genus or species as the glucoamylase. A signal sequence and a promoter sequence comprising a DNA construct or vector can be introduced into a fungal host cell and can be derived from the same source. For example, the signal sequence may be the *Trichoderma reesei* cbh1 signal sequence, which is operably linked to a cbh1 promoter.

An expression vector may also comprise a suitable transcription terminator and, in eukaryotes, polyadenylation sequences operably linked to the DNA sequence encoding a glucoamylase. Termination and polyadenylation sequences may suitably be derived from the same sources as the promoter.

The vector may also comprise a selectable marker, e.g., a gene the product of which complements a defect in the isolated host cell, such as the dal genes from *B. subtilis* or *B. licheniformis*, or a gene that confers antibiotic resistance such as, e.g., ampicillin, kanamycin, chloramphenicol or tetracycline resistance. Furthermore, the vector may comprise *Aspergillus* selection markers such as amdS, argB, and niaD a marker giving rise to hygromycin resistance, or the selection may be accomplished by co-transformation, such as known in the art. See e.g., Published International PCT Application WO 91/17243.

Intracellular expression may be advantageous in some respects, e.g., when using certain bacteria or fungi as host cells to produce large amounts of alpha-glucosidase for subsequent enrichment or purification. Alternatively, extracellular secretion of glucoamylase into the culture medium can also be used to make a cultured cell material comprising the isolated glucoamylase.

The procedures used to ligate the DNA construct encoding a glucoamylase, the promoter, terminator and other elements, respectively, and to insert them into suitable vectors containing the information necessary for replication, are known to persons skilled in the art and readily available. See, e.g., Sambrook et al., MOLECULAR CLONING: A LABORATORY MANUAL, $2^{nd}$ ed., Cold Spring Harbor, 1989, and $3^{rd}$ ed., 2001.

An isolated cell, either comprising a DNA construct or an expression vector, is advantageously used as a host cell in the recombinant production of a glucoamylase. The cell may be transformed with the DNA construct encoding the enzyme, conveniently by integrating the DNA construct (in one or more copies) in the host chromosome. This integration is generally considered to be an advantage, as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector in connection with the different types of host cells.

Examples of suitable bacterial host organisms are Gram positive bacterial species such as Bacillaceae including *Bacillus subtilis*, *Bacillus licheniformis*, *Bacillus lentus*, *Bacillus brevis*, *Geobacillus* (formerly *Bacillus*) *stearothermophilus*, *Bacillus alkalophilus*, *Bacillus amyloliquefaciens*, *Bacillus coagulans*, *Bacillus lautus*, *Bacillus megaterium*, and *Bacillus thuringiensis*; *Streptomyces* species such as *Streptomyces murinus*; lactic acid bacterial species including *Lactococcus* sp. such as *Lactococcus lactis*; *Lactobacillus* sp. including *Lactobacillus reuteri*; *Leuconostoc* sp.; *Pediococcus* sp.; and *Streptococcus* sp. Alternatively, strains of a Gram negative bacterial species belonging to Enterobacteriaceae including *E. coli*, or to Pseudomonadaceae can be selected as the host organism.

A suitable yeast host organism can be selected from the biotechnologically relevant yeasts species such as but not limited to yeast species such as *Pichia* sp., *Hansenula* sp., or *Kluyveromyces*, *Yarrowinia*, *Schizosaccharomyces* species or a species of *Saccharomyces*, including *Saccharomyces cerevisiae* or a species belonging to *Schizosaccharomyces* such as, for example, *S. pombe* species. A strain of the methylotrophic yeast species, *Pichia pastoris*, can be used as the host organism. Alternatively, the host organism can be a *Hansenula* species.

Suitable host organisms among filamentous fungi include species of *Aspergillus*, e.g., *Aspergillus niger*, *Aspergillus oryzae*, *Aspergillus tubigensis*, *Aspergillus awamori*, or *Aspergillus nidulans*. Alternatively, strains of a *Fusarium* species, e.g., *Fusarium oxysporum* or of a *Rhizomucor* species such as *Rhizomucor miehei* can be used as the host organism. Other suitable strains include *Thermomyces* and *Mucor* species. In addition, *Trichoderma* sp. can be used as a host. A glucoamylase expressed by a fungal host cell can be glycosylated, i.e., will comprise a glycosyl moiety. The glycosylation pattern can be the same or different as present in the wild-type glucoamylase. The type and/or degree of glycosylation may impart changes in enzymatic and/or biochemical properties.

It is advantageous to delete genes from expression hosts, where the gene deficiency can be cured by the transformed expression vector. Known methods may be used to obtain a fungal host cell having one or more inactivated genes. Any gene from a *Trichoderma* sp. or other filamentous fungal host that has been cloned can be deleted, for example, cbh1, cbh2, egl1, and egl2 genes. Gene deletion may be accomplished by inserting a form of the desired gene to be inactivated into a plasmid by methods known in the art.

Introduction of a DNA construct or vector into a host cell includes techniques such as transformation; electroporation; nuclear microinjection; transduction; transfection, e.g., lipofection mediated and DEAE-Dextrin mediated transfection; incubation with calcium phosphate DNA precipitate; high velocity bombardment with DNA-coated microprojectiles; and protoplast fusion. General transformation techniques are known in the art. See, e.g., Sambrook et al. (2001), supra. The expression of heterologous protein in *Trichoderma* is described, for example, in U.S. Pat. No. 6,022,725. Reference is also made to Cao et al. (2000) *Science* 9:991-1001 for transformation of *Aspergillus* strains. Genetically stable transformants can be constructed with vector systems whereby the nucleic acid encoding an alpha-glucosidase is stably integrated into a host cell chromosome. Transformants are then selected and purified by known techniques.

A method of producing a glucoamylase may comprise cultivating a host cell under conditions conducive to the production of the enzyme and recovering the enzyme from the cells and/or culture medium.

The medium used to cultivate the cells may be any conventional medium suitable for growing the host cell and obtaining expression of a glucoamylase polypeptide. Suitable media and media components are available from commercial suppliers or may be prepared according to published recipes (e.g., as described in catalogues of the American Type Culture Collection).

Any of the fermentation methods well known in the art can suitably used to ferment the transformed or the derivative fungal strain as described above. In some embodiments, fungal cells are grown under batch or continuous fermentation conditions.

Separation and concentration techniques are known in the art and conventional methods can be used to prepare a concentrated solution or broth comprising a glucoamylase polypeptide of the invention.

After fermentation, a fermentation broth is obtained, the microbial cells and various suspended solids, including residual raw fermentation materials, are removed by conventional separation techniques in order to obtain a glucoamylase solution. Filtration, centrifugation, microfiltration, rotary vacuum drum filtration, ultrafiltration, centrifugation followed by ultra-filtration, extraction, or chromatography, or the like, are generally used.

It may at times be desirable to concentrate a solution or broth comprising a glucoamylase polypeptide to optimize recovery. Use of un-concentrated solutions or broth would typically increase incubation time in order to collect the enriched or purified enzyme precipitate.

The present invention also relates to compositions comprising a polypeptide of the present invention. In some embodiments, a polypeptide comprising an amino acid sequence having preferably at least 83%, at least 85%, at least 90%, at least 92%, at least 93%, at least 94%, at least 95%, at least 96%, at least 97%, at least 98%, and even at least 99%, amino acid sequence identity to the polypeptide of SEQ ID NO: 7, 8, or 9, and having glucoamylase activity can also be used in the enzyme composition. Preferably, the compositions are formulated to provide desirable characteristics such as low color, low odor and acceptable storage stability. polypeptides The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, alpha-glucosidase, beta-glucosidase, beta-amylase, isoamylase, haloperoxidase, invertase, laccase, lipase, lysozyme, mannosidase, oxidase, pectinolytic enzyme, peptidoglutaminase, peroxidase, phytase, polyphenoloxidase, proteolytic enzyme, pullulanase, ribonuclease, transglutaminase, xylanase or a combination thereof, which may be added in effective amounts well known to the person skilled in the art.

The polypeptide compositions may be prepared in accordance with methods known in the art and may be in the form of a liquid or a dry composition. For instance, the compositions comprising the present glucoamylases may be aqueous or non-aqueous formulations, granules, powders, gels, slurries, pastes, etc., which may further comprise any one or more of the additional enzymes listed, herein, along with buffers, salts, preservatives, water, co-solvents, surfactants, and the like. Such compositions may work in combination with endogenous enzymes or other ingredients already present in a slurry, water bath, washing machine, food or drink product, etc, for example, endogenous plant (including algal) enzymes, residual enzymes from a prior processing step, and the like. The polypeptide to be included in the composition may be stabilized in accordance with methods known in the art.

The composition may be cells expressing the polypeptide, including cells capable of producing a product from fermentation. Such cells may be provided in a cream or in dry form along with suitable stabilizers. Such cells may further express additional polypeptides, such as those mentioned, above.

Examples are given below of preferred uses of the polypeptides or compositions of the invention. The dosage of the polypeptide composition of the invention and other conditions under which the composition is used may be determined on the basis of methods known in the art.

The present invention is also directed to use of a polypeptide or composition of the present invention in a liquefaction, a saccharification and/or a fermentation process. The polypeptide or composition may be used in a single process, for example, in a liquefaction process, a saccharification process, or a fermentation process. The polypeptide or composition may also be used in a combination of processes for example in a liquefaction and saccharification process, in a liquefaction and fermentation process, or in a saccharification and fermentation process, preferably in relation to starch conversion.

The liquefied starch may be saccharified into a syrup rich in lower DP (e.g., DP1+DP2) saccharides, using alpha-amylases and glucoamylases, optionally in the presence of another enzyme(s). The exact composition of the products of saccharification depends on the combination of enzymes used, as well as the type of starch processed. Advantageously, the syrup obtainable using the provided glucoamylases may contain a weight percent of DP2 of the total oligosaccharides in the saccharified starch exceeding 30%, e.g., 45%-65% or 55%-65%. The weight percent of (DP1+DP2) in the saccharified starch may exceed about 70%, e.g., 75%-85% or 80%-85%.

Whereas liquefaction is generally run as a continuous process, saccharification is often conducted as a batch process. Saccharification conditions are dependent upon the nature of the liquefact and type of enzymes available. In some cases, a saccharification process may involve temperatures of about 60-65° C. and a pH of about 4.0-4.5, e.g., pH 4.3. Saccharification may be performed, for example, at a temperature between about 40° C., about 50° C., or about 55° C. to about 60° C. or about 65° C., necessitating cooling of the liquefact. The pH may also be adjusted as needed. Saccharification is normally conducted in stirred tanks, which may take several hours to fill or empty. Enzymes typically are added either at a fixed ratio to dried solids, as the tanks are filled, or added as a single dose at the commencement of the filling stage. A saccharification reaction to make a syrup typically is run over about 24-72 hours, for example, 24-48 hours. However, it is common only to do a pre-saccharification of typically 40-90 minutes at a temperature between 30-65° C., typically about 60° C., followed by complete saccharification in a simultaneous saccharification and fermentation (SSF). In one embodiment, a process of the invention includes pre-saccharifying starch-containing material before simultaneous saccharification and fermentation (SSF) process. The pre-saccharification can be carried out at a high temperature (for example, 50-85° C., preferably 60-75° C.) before moving into SSF. Preferredly, saccharification optimally is conducted at a higher temperature range of about 30° C. to about 75° C., e.g., 45°

C.-75° C. or 50° C.-75° C. By conducting the saccharification process at higher temperatures, the process can be carried out in a shorter period of time or alternatively the process can be carried out using lower enzyme dosage. Furthermore, the risk of microbial contamination is reduced when carrying the liquefaction and/or saccharification process at higher temperature.

In a preferred aspect of the present invention, the liquefaction and/or saccharification includes sequentially or simultaneously performed liquefaction and saccharification processes.

The soluble starch hydrolysate, particularly a glucose rich syrup, can be fermented by contacting the starch hydrolysate with a fermenting organism typically at a temperature around 32° C., such as from 30° C. to 35° C. "Fermenting organism" refers to any organism, including bacterial and fungal organisms, suitable for use in a fermentation process and capable of producing desired a fermentation product. Especially suitable fermenting organisms are able to ferment, i.e., convert, sugars, such as glucose or maltose, directly or indirectly into the desired fermentation product. Examples of fermenting organisms include yeast, such as *Saccharomyces cerevisiae* and bacteria, e.g., *Zymomonas mobilis*, expressing alcohol dehydrogenase and pyruvate decarboxylase. The ethanologenic microorganism can express xylose reductase and xylitol dehydrogenase, which convert xylose to xylulose. Improved strains of ethanologenic microorganisms, which can withstand higher temperatures, for example, are known in the art and can be used. See Liu et al. (2011) *Sheng Wu Gong Cheng Xue Bao* 27:1049-56. Commercially available yeast includes, e.g., Red Star™/Lesaffre Ethanol Red (available from Red Star/Lesaffre, USA) FALI (available from Fleischmann's Yeast, a division of Burns Philp Food Inc., USA), SUPERSTART (available from Alltech), GERT STRAND (available from Gert Strand AB, Sweden), SYNERXIA® ADY (available from DuPont), SYNERXIA® THRIVE (available from DuPont), FERMIOL (available from DSM Specialties). The temperature and pH of the fermentation will depend upon the fermenting organism. Microorganisms that produce other metabolites, such as citric acid and lactic acid, by fermentation are also known in the art. See, e.g., Papagianni (2007) *Biotechnol. Adv.* 25:244-63; John et al. (2009) *Biotechnol. Adv.* 27:145-52.

The saccharification and fermentation processes may be carried out as an SSF process. An SSF process can be conducted with fungal cells that express and secrete glucoamylase continuously throughout SSF. The fungal cells expressing glucoamylase also can be the fermenting microorganism, e.g., an ethanologenic microorganism. Ethanol production thus can be carried out using a fungal cell that expresses sufficient glucoamylase so that less or no enzyme has to be added exogenously. The fungal host cell can be from an appropriately engineered fungal strain. Fungal host cells that express and secrete other enzymes, in addition to glucoamylase, also can be used. Such cells may express amylase and/or a pullulanase, phytase, alpha-glucosidase, isoamylase, beta-amylase cellulase, xylanase, other hemicellulases, protease, beta-glucosidase, pectinase, esterase, redox enzymes, transferase, or other enzymes. Fermentation may be followed by subsequent recovery of ethanol.

In accordance with the present invention the fermentation includes, without limitation, fermentation processes used to produce alcohols (e.g., ethanol, methanol, butanol); organic acids (e.g., citric acid, acetic acid, itaconic acid, lactic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In such preferred embodiment, the process is typically carried at a temperature between 28° C. and 36° C., such as between 29° C. and 35° C., such as between 30° C. and 34° C., such as around 32° C., at a pH in the range between 3 and 7, preferably from pH 3.5 to 6, or more preferably from pH 4 to 5.

In other embodiments, low pH values will minimize the risk of contamination, since competing organisms are no longer able to grow. The fermentation process of the invention may be carried out at low pH, for instance fermentation of organic acids, as typically fermentation organisms lower the pH rapidly to about 4.0 to 4.5, and some of the lactobacilli even lower the pH to about 3.5. The amount of free lactic acid present in a solution (eg. at least about 50 g/L, preferably at least about 80 g/L, and more preferably at least about 100 g/L lactate) results in a relatively low pH. The higher the percentage of the lactate which is present in its free acid form, the lower the solution pH. For example, where the medium pH is equal to the pKa of lactic acid (about 3.8), 50% of the lactate is present in the free acid form. At pH 4.2, about 31% of the lactate as a free acid and at pH 4.0 and 3.9, about 41% and 47% respectively of the The present invention provides a use of the glucoamylase(s) of the invention for producing glucose and other saccharides from raw starch or granular starch. Generally, glucoamylase of the present invention either alone or in the presence of an alpha-amylase can be used in raw starch hydrolysis (RSH) or granular starch hydrolysis (GSH) process for producing desired sugars and fermentation products. The granular starch is solubilized by enzymatic hydrolysis below the gelatinization temperature. Such "low-temperature" systems (known also as "no-cook" or "cold-cook") have been reported to be able to process higher concentrations of dry solids than conventional systems (e.g., up to 45%).

A "raw starch hydrolysis" process (RSH) differs from conventional starch treatment processes, including sequentially or simultaneously saccharifying and fermenting granular starch at or below the gelatinization temperature of the starch substrate typically in the presence of at least an glucoamylase and/or amylase. Starch heated in water begins to gelatinize between 50° C. and 75° C., the exact temperature of gelatinization depends on the specific starch. For example, the gelatinization temperature may vary according to the plant species, to the particular variety of the plant species as well as with the growth conditions. In the context of this invention the gelatinization temperature of a given starch is the temperature at which birefringence is lost in 5% of the starch granules using the method described by Gorinstein. S. and Lii. C., Starch/Starke, Vol. 44 (12) pp. 461-466 (1992).

The glucoamylase of the invention may also be used in combination with an enzyme that hydrolyzes only alpha-(1, 6)-glucosidic bonds in molecules comprising at least four glucosyl residues. Preferably, the glucoamylase of the invention is used in combination with pullulanase or isoamylase. The use of isoamylase and pullulanase for debranching of starch, the molecular properties of the enzymes, and the potential use of the enzymes together with glucoamylase is described in G. M. A. van Beynum et al., Starch Conversion Technology, Marcel Dekker, New York, 1985, 101-142.

The term "fermentation product" means a product produced by a process including a fermentation process using a fermenting organism. Fermentation products contemplated according to the invention include alcohols (e.g., arabinitol, butanol, ethanol, glycerol, methanol, ethylene glycol, propylene glycol, butanediol, glycerin, sorbitol, and xylitol); organic acids (e.g., acetic acid, acetonic acid, adipic acid, ascorbic acid, citric acid, 2,5-diketo-D-gluconic acid, formic acid, fumaric acid, glutaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); ketones (e.g., acetone); amino acids (e.g., aspartic acid, glutamic acid, glycine, lysine, serine, and threonine); an alkane (e.g., pentane, hexane, heptane, octane, nonane, decane, undecane, and dodecane); a cycloalkane (e.g., cyclopentane, cyclohexane, cycloheptane, and cyclooctane); an alkene (e.g. pentene, hexene, heptene, and octene); gases (e.g., methane, hydrogen ($H_2$), carbon dioxide ($CO_2$), and carbon monoxide (CO)); antibiotics (e.g., penicillin and tetracycline); enzymes; vitamins (e.g., riboflavin, $B_{12}$, beta-carotene); and hormones.

In a preferred aspect, the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, high-alcohol beer, low-alcohol beer, low-calorie beer or light beer. Preferred fermentation processes used include alcohol fermentation processes, which are well known in the art. Preferred fermentation processes are anaerobic fermentation processes, which are well known Processes for making beer are well known in the art. See, e.g., Wolfgang Kunze (2004) "Technology Brewing and Malting," Research and Teaching Institute of Brewing, Berlin (VLB), 3rd edition. Briefly, the process involves: (a) preparing a mash, (b) filtering the mash to prepare a wort, and (c) fermenting the wort to obtain a fermented beverage, such as beer.

The brewing composition comprising a glucoamylase, in combination with an amylase and optionally a pullulanase and/or isoamylase, may be added to the mash of step (a) above, i.e., during the preparation of the mash. Alternatively, or in addition, the brewing composition may be added to the mash of step (b) above, i.e., during the filtration of the mash. Alternatively, or in addition, the brewing composition may be added to the wort of step (c) above, i.e., during the fermenting of the wort.

In still another aspect, the glucoamylases described herein can be used as a feed additive for animals to increase starch digestibility. Describe herein is a method for increasing starch digestibility in an animal which comprises adding at least one glucoamylase selected from the group consisting of:

(g) a polypeptide having the amino acid sequence of SEQ ID NO: 7, 8, or 9;
(h) a polypeptide having at least 83% identity to the amino acid sequence of SEQ ID NO: 7, 8, or 9;
(i) a polypeptide having at least 83% identity to a catalytic domain of SEQ ID NO: 7, 8, or 9;
(j) a polypeptide having at least 83% identity to a linker and a catalytic domain of SEQ ID NO: 7, 8, or 9; or
(k) a mature polypeptide produced by the processing of the polypeptide of SEQ ID NO: 1, 2, or 3 by a signal peptidase or post translational modification during secretion from an expression host;

as a feed additive to feed for an animal wherein said glucoamylase (a) has at least 20% activity or at least 20% greater residual activity at pH less than or equal to 3 in the presence of pepsin or rumin fluid (e.g., pepsin-containing rumen fluid) as compared to activity of the enzymes at pH 6 alone or in the presence of or rumin fluid (e.g., pepsin-containing rumen fluid), and (b) the enzyme works with pancreatic amylase to increase glucose yield.

In another aspect, when the animal is a ruminant then the enzyme is active in at least two of three digestive chambers of a ruminant comprising a rumen, an abomasum and a small intestine. The rumen is the largest compartment, with a volume of 150-200 litres (40-50 gallons).

Ruminants have the unique ability to convert roughage into protein and energy through their microbial/enzyme digestive systems. Accordingly, ruminants play an important role in the earth's ecology and in the food chain.

The primary difference between a ruminant and a non-ruminant is that a ruminant has a four-compartment stomach consisting of a rumen, reticulum, omasum and abomasum. The abomasum is the direct equivalent of the monogastric stomach (McDonald et al., 2011, Animal Nutrition (7th Edition), pages 156-191).

In the digestive system, there are billions of microorganisms. They help the cow to digest and utilize nutrients in the feed. To achieve efficient feed utilization and high milk yield, the bacteria must have optimal conditions. It is the bacteria that digest the feed. Feeding a cow, in fact, involves feeding the micro-organisms in her rumen. The process of fermentation takes place in the rumen and the reticulum. The cow's rumen is like a large fermentation vat. More than 200 different bacteria and 20 types of protozoa help the cow to utilize fibrous feedstuffs and non-protein nitrogen sources. Fermentation is the chemical process by which molecules such as glucose are broken down anaerobically, such as when microorganisms convert carbohydrates into volatile fatty acids and gases. This process allows the cow to convert cellulosic fiber into energy. Of gases produced within the rumen during fermentation (500-1500 litres per day) (150-400 gallons), 20-40% consist of methane and carbon dioxide. Production of fermentation gases represents a considerable energy loss. Certain fermentation modifiers, such as ionophores, improve energy efficiency of ruminants by reducing those gas energy losses.

The rumen and reticulum are basically one compartment, but with different functions. While much of fermentative action occurs in the rumen, the reticulum serves as a staging area for passage into the omasum or regurgitation.

The ideal rumen pH value is between 6 and 7. The ruminal microorganisms are healthiest within this range. If the pH value varies too much, some types of micro-organisms are eliminated, and there is reduced utilization of the feed. Micro-organisms that digest cellulose (hay, silage, etc.) are unable to grow or ferment cellulose with a pH value below 6.0. When ruminal pH drops below 6, the rumen is considered to be acidotic. Ruminal acidosis can be acute with a rapid, severe drop in pH. More common in high producing herds is sub-clinical acidosis which is characterized by chronic, intermittent periods of low ruminal pH.

As noted above, the digestibility of starch in feeds is highly variable and dependent on a number of factors including the physical structure of both the starch and feed matrix.

It has been found that starch digestibility in an animal's diet can be improved by the use of at least one glucoamylase as a feed additive for a ruminant wherein said glucoamylase: (a) has at least 20% activity (such as at least about 25%, 30%, 35%, 40%, 45%, 50%, 55%, 60%, 65%, 70%, 75%, or 80% greater activity, inclusive of all values in between these percentages) or at least 20% greater residual activity (such as at least about 25%, 30%, 35%, 40%, 45%, 50%, 55%, 60%, 65%, 70%, 75%, or 80% greater residual activity, inclusive of all values in between these percentages) at pH less than or equal to 3 in the presence of pepsin or rumin fluid (e.g., pepsin-containing rumen fluid) as compared to activity of the enzymes at pH 6 alone or in the presence of or rumin fluid (e.g., pepsin-containing rumen fluid) and (b) the hydrolase works with digestive enzymes present in the digestive chambers of the animal to increase glucose yield and increase starch digestibility.

Any of the glucoamylases described herein may be used alone or in combination with at least one direct fed microbial. Categories of DFMs include *Bacillus*, Lactic Acid Bacteria and Yeasts. Bacilli are unique, gram-positive rods that form spores. These spores are very stable and can withstand environmental conditions such as heat, moisture and a range of pH. These spores germinate into active vegetative cells when ingested by an animal and can be used in meal and pelleted diets.

The terms "animal feed," "feed", "feedstuff" and "fodder" are used interchangeably and can comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grains with Solubles (DDGS) (particularly corn based Distillers Dried Grains with Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; and/or e) minerals and vitamins.

When used as, or in the preparation of a feed, such as functional feed, the enzyme or feed additive composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient. For example, there could be mentioned at least one component selected from the group consisting of a protein, a peptide, sucrose, lactose, sorbitol, glycerol, propylene glycol, sodium chloride, sodium sulfate, sodium acetate, sodium citrate, sodium formate, sodium sorbate, potassium chloride, potassium sulfate, potassium acetate, potassium citrate, potassium formate, potassium acetate, potassium sorbate, magnesium chloride, magnesium sulfate, magnesium acetate, magnesium citrate, magnesium formate, magnesium sorbate, sodium metabisulfite, methyl paraben and propyl paraben.

In a preferred embodiment, the enzyme or feed additive composition of the present invention is admixed with a feed component to form a feedstuff. The term "feed component" as used herein means all or part of the feedstuff. Part of the feedstuff may mean one constituent of the feedstuff or more than one constituent of the feedstuff, e.g. 2 or 3 or 4 or more. In one embodiment, the term "feed component" encompasses a premix or premix constituents. Preferably, the feed may be a fodder, or a premix thereof, a compound feed, or a premix thereof.

A feed additive composition according to the present invention may be admixed with a compound feed, a compound feed component or to a premix of a compound feed or to a fodder, a fodder component, or a premix of a fodder.

Any feedstuff described herein may comprise one or more feed materials selected from the group comprising a) cereals, such as small grains (e.g., wheat, barley, rye, oats, triticale and combinations thereof) and/or large grains such as maize or sorghum; b) by products from cereals, such as corn gluten meal, wet-cake (particularly corn based wet-cake), Distillers Dried Grains (DDG) (particularly corn based Distillers Dried Grains (cDDG)), Distillers Dried Grains with Solubles (DDGS) (particularly corn based Distillers Dried Grains with Solubles (cDDGS)), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

The term "compound feed" means a commercial feed in the form of a meal, a pellet, nuts, cake or a crumble. Compound feeds may be blended from various raw materials and additives. These blends are formulated according to the specific requirements of the target animal.

Compound feeds can be complete feeds that provide all the daily required nutrients, concentrates that provide a part of the ration (protein, energy) or supplements that only provide additional micronutrients, such as minerals and vitamins.

The main ingredients used in compound feed are the feed grains, which include corn, wheat, canola meal, rapeseed meal, lupin, soybeans, sorghum, oats, and barley.

Suitably a premix as referred to herein may be a composition composed of microingredients such as vitamins, minerals, chemical preservatives, antibiotics, fermentation products, and other essential ingredients. Premixes are usually compositions suitable for blending into commercial rations.

In one embodiment, the feedstuff comprises or consists of corn, DDGS (such as cDDGS), wheat, wheat bran or any combination thereof.

In one embodiment, the feed component may be corn, DDGS (e.g. cDDGS), wheat, wheat bran or a combination thereof. In one embodiment, the feedstuff comprises or consists of corn, DDGS (such as cDDGS) or a combination thereof.

A feedstuff described herein may contain at least 30%, at least 40%, at least 50% or at least 60% by weight corn and soybean meal or corn and full fat soy, or wheat meal or sunflower meal.

For example, a feedstuff may contain between about 5 to about 40% corn DDGS. For poultry, the feedstuff on average may contain between about 7 to 15% corn DDGS. For swine (pigs), the feedstuff may contain on average 5 to 40% corn DDGS. It may also contain corn as a single grain, in which case the feedstuff may comprise between about 35% to about 80% corn.

The feed may be one or more of the following: a compound feed and premix, including pellets, nuts or (cattle) cake; a crop or crop residue: corn, soybeans, sorghum, oats, barley copra, straw, chaff, sugar beet waste; fish meal; meat and bone meal; molasses; oil cake and press cake; oligosaccharides; conserved forage plants: silage; seaweed; seeds and grains, either whole or prepared by crushing, milling etc.; sprouted grains and legumes; yeast extract.

The term "feed" as used herein encompasses in some embodiments pet food. A pet food is plant or animal material intended for consumption by pets, such as dog food or cat food. Pet food, such as dog and cat food, may be either in a dry form, such as kibble for dogs, or wet canned form. Cat food may contain the amino acid taurine.

As used herein the term "contacted" refers to the indirect or direct application of a glucoamylase as described herein (or a composition comprising a glucoamylase) to a product (e.g. the feed). Examples of application methods which may be used, include, but are not limited to, treating the product in a material comprising the feed additive composition, direct application by mixing the feed additive composition with the product, spraying the feed additive composition onto the product surface or dipping the product into a preparation of the feed additive composition. In one embodiment, the feed additive composition of the present invention is preferably admixed with the product (e.g. feedstuff). Alternatively, the feed additive composition may be included in the emulsion or raw ingredients of a feedstuff. This allows the composition to impart a performance benefit.

It is also possible that at least one glucoamylase (or an enzyme composition comprising at least one glucoamylase as described herein) described herein can be homogenized to produce a powder.

In an alternative preferred embodiment, an enzyme composition comprising at least one glucoamylase can be formulated to granules as described in WO2007/044968 (referred to as TPT granules) or WO1997/016076 or WO1992/012645 incorporated herein by reference. "TPT" means Thermo Protection Technology.

In another aspect, when the feed additive composition is formulated into granules the granules comprise a hydrated barrier salt coated over the protein core. The advantage of such salt coating is improved thermo-tolerance, improved storage stability and protection against other feed additives otherwise having adverse effect on the enzyme. Preferably, the salt used for the salt coating has a water activity greater than 0.25 or constant humidity greater than 60% at 20° C. In some embodiments, the salt coating comprises $Na_2SO_4$.

A method of preparing at least one glucoamylase as described herein (or an enzyme composition comprising at least one glucoamylase as described herein) may also comprise the further step of pelleting the powder. The powder may be mixed with other components known in the art. The powder, or mixture comprising the powder, may be forced through a die and the resulting strands are cut into suitable pellets of variable length.

Optionally, the pelleting step may include a steam treatment, or conditioning stage, prior to formation of the pellets. The mixture comprising the powder may be placed in a conditioner, e.g. a mixer with steam injection. The mixture is heated in the conditioner up to a specified temperature, such as from 60-100° C., typical temperatures would be 70° C., 80° C., 85° C., 90° C. or 95° C. The residence time can be variable from seconds to minutes and even hours. Such as 5 seconds, 10 seconds, 15 seconds, 30 seconds, 1 minutes 2 minutes, 5 minutes, 10 minutes, 15 minutes, 30 minutes and 1 hour. It will be understood that a glycoside hydrolase as described herein (or an enzyme composition comprising a glycoside hydrolase as described herein) are suitable for addition to any appropriate feed material.

Optionally, the feedstuff may also contain additional minerals such as, for example, calcium and/or additional vitamins. In some embodiments, the feedstuff is a corn soybean meal mix.

Feedstuff is typically produced in feed mills in which raw materials are first ground to a suitable particle size and then mixed with appropriate additives. The feedstuff may then be produced as a mash or pellets; the later typically involves a method by which the temperature is raised to a target level and then the feed is passed through a die to produce pellets of a particular size. The pellets are allowed to cool. Subsequently liquid additives such as fat and enzyme may be added. Production of feedstuff may also involve an additional step that includes extrusion or expansion prior to pelleting, in particular by suitable techniques that may include at least the use of steam.

The feed additive composition and/or the feedstuff comprising the same may be used in any suitable form. The feed additive composition may be used in the form of solid or liquid preparations or alternatives thereof. Examples of solid preparations include powders, pastes, boluses, capsules, pellets, tablets, dusts, and granules which may be wettable, spray-dried or freeze-dried. Examples of liquid preparations include, but are not limited to, aqueous, organic or aqueous-organic solutions, suspensions and emulsions.

Preferably, a food or feed additive composition may comprise at least one physiologically acceptable carrier. The physiologically acceptable carrier is preferably selected from at least one of maltodextrin, limestone (calcium carbonate), cyclodextrin, wheat or a wheat component, sucrose, starch, $Na_2SO_4$, Talc, PVA and mixtures thereof. In a further embodiment, the food or feed additive may further comprise a metal ion chelator. The metal ion chelator may be selected from EDTA or citric acid.

In some embodiments, the food or feed additive composition comprises a glycoside hydrolase as described herein at a level of at least 0.0001 g/kg, 0.001 g/kg, at least 0.01 g/kg, at least 0.1 g/kg, at least 1 g/kg, at least 5 g/kg, at least 7.5 g/kg, at least 10.0 g/kg, at least 15.0 g/kg, at least 20.0 g/kg, at least 25.0 g/kg. In some embodiments, the food or feed additive comprises at a level such that when added to a food or feed material, the feed material comprises a glycoside hydrolase as described herein in a range of 1-500 mg/kg, 1-100 mg/kg, 2-50 mg/kg or 2-10 mg/kg. In some embodiments of the present invention the food or feed material comprises at least 100, 1000, 2000, 3000, 4000, 5000, 10000, 20000, 30000, 50000, 100000, 500000, 1000000 or 2000000 Units of glycoside hydrolase per kilogram feed or food material.

Formulations comprising any of the at least one glucoamylase described herein and compositions described herein may be made in any suitable way to ensure that the formulation comprises active enzymes. Such formulations may be as a liquid, a dry powder or a granule. Preferably, the feed additive composition is in a solid form suitable for adding on or to a feed pellet.

In one embodiment animal feed may be formulated to a granule for feed compositions comprising: a core; an active agent; and at least one coating, the active agent of the granule retaining at least 50% activity, at least 60% activity, at least 70% activity, at least 80% activity after conditions selected from one or more of a) a feed pelleting process, b) a steam-heated feed pretreatment process, c) storage, d) storage as an ingredient in an unpelleted mixture, and e) storage as an ingredient in a feed base mix or a feed premix comprising at least one compound selected from trace minerals, organic acids, reducing sugars, vitamins, choline chloride, and compounds which result in an acidic or a basic feed base mix or feed premix.

Regarding the granule, at least one coating may comprise a moisture hydrating material that constitutes at least 55% w/w of the granule; and/or at least one coating may comprise two coatings. The two coatings may be a moisture hydrating coating and a moisture barrier coating. In some embodiments, the moisture hydrating coating may be between 25% and 60% w/w of the granule and the moisture barrier coating may be between 2% and 15% w/w of the granule. The moisture hydrating coating may be selected from inorganic salts, sucrose, starch, and maltodextrin and the moisture barrier coating may be selected from polymers, gums, whey and starch.

The granule may be produced using a feed pelleting process and the feed pretreatment process may be conducted between 70° C. and 95° C. for up to several minutes, such as between 85° C. and 95° C.

The granule may have a moisture barrier coating selected from polymers and gums and the moisture hydrating material may be an inorganic salt. The moisture hydrating coating may be between 25% and 45% w/w of the granule and the moisture barrier coating may be between 2% and 10% w/w of the granule.

Alternatively, the composition is in a liquid formulation suitable for consumption preferably such liquid consumption contains one or more of the following: a buffer, salt, sorbitol and/or glycerol.

Also, the feed additive composition may be formulated by applying, e.g. spraying, the enzyme(s) onto a carrier substrate, such as ground wheat for example.

In one embodiment, the feed additive composition may be formulated as a premix. By way of example only the premix may comprise one or more feed components, such as one or more minerals and/or one or more vitamins.

In some embodiments, at least one glucoamylase will be in a physiologically acceptable carrier. Suitable carriers may be large, slowly metabolized macromolecules such as proteins, polypeptides, liposomes, polysaccharides, polylactic acids, polyglycolic acids, polymeric amino acids, amino acid copolymers and inactive virus particles. Pharmaceutically acceptable salts can be used, for example mineral acid salts, such as hydrochlorides, hydrobromides, phosphates and sulphates, or salts of organic acids, such as acetates, propionates, malonates and benzoates. Once formulated, the compositions of the invention can be administered directly to the ruminant.

Additionally, the glucoamylase-containing compositions disclosed herein can be further formulated with (e.g., blended with) one or more additional component enzymes (e.g. further feed enzymes or brewing or malting enzymes, or grain processing enzymes or wheat gluten-starch separation enzymes).

Suitable additional enzymes for use in the glucoamylase-containing compositions disclosed herein can be one or more of the enzymes selected from the group consisting of: endoglucanases (E.C. 3.2.1.4); celliobiohydrolases (E.C. 3.2.1.91), (β-glucosidases (E.C. 3.2.1.21), cellulases (E.C. 3.2.1.74), lichenases (E.C. 3.1.1.73), lipases (E.C. 3.1.1.3), lipid acyltransferases (generally classified as E.C. 2.3.1.x), phospholipases (E.C. 3.1.1.4, E.C. 3.1.1.32 or E.C. 3.1.1.5), phytases (e.g. 6-phytase (E.C. 3.1.3.26) or a 3-phytase (E.C. 3.1.3.8), alpha-amylases (E.C. 3.2.1.1), other xylanases (E.C. 3.2.1.8, E.C. 3.2.1.32, E.C. 3.2.1.37, E.C. 3.1.1.72, E.C. 3.1.1.73), glucoamylases (E.G. 3.2.1.3), proteases (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)) and/or mannanases (e.g. a β-mannanase (E.C. 3.2.1.78)).

In one embodiment (e.g., for feed applications) the other component enzyme can be one or more of the enzymes selected from the group consisting of an amylase (including α-amylases (E.C. 3.2.1.1), G4-forming amylases (E.C. 3.2.1.60), β-amylases (E.C. 3.2.1.2) and γ-amylases (E.C. 3.2.1.3); and/or a protease (e.g. subtilisin (E.C. 3.4.21.62) or a bacillolysin (E.C. 3.4.24.28) or an alkaline serine protease (E.C. 3.4.21.x) or a keratinase (E.C. 3.4.x.x)).

In one embodiment (e.g., for feed applications) the other component enzyme may be a combination of an amylase (e.g. α-amylases (E.C. 3.2.1.1)) and a protease (e.g. subtilisin (E.C. 3.4.21.62)).

In one embodiment (e.g., for feed applications) the other component enzyme can be a β-glucanase, e.g. an endo-1,3 (4)-β-glucanases (E.C. 3.2.1.6).

In one embodiment (e.g., for feed applications) the other component enzyme can be a mannanases (e.g. a β-mannanase (E.C. 3.2.1.78)).

In one embodiment (e.g., for feed applications) the other component enzyme can be a lipase (E.C. 3.1.1.3), a lipid acyltransferase (generally classified as E.C. 2.3.1.x), or a phospholipase (E.C. 3.1.1.4, E.C. 3.1.1.32 or E.C. 3.1.1.5), suitably a lipase (E.C. 3.1.1.3).

In one embodiment (particularly for feed applications) the other component enzyme may be a serine protease (e.g. E.C. 3.4.21, subtilisin), trypsin-like S1 or S2 proteases, or a metalloprotease (e.g. E.C. 3.4.24, bacillolysin), or an aspartyl protease (e.g. E.C. 3.4.23).

EXAMPLES

Unless defined otherwise herein, all technical and scientific terms used herein have the same meaning as commonly understood by one of ordinary skill in the art to which this disclosure belongs. Singleton, et al., *DICTIONARY OF MICROBIOLOGY AND MOLECULAR BIOLOGY, 2D ED.*, John Wiley and Sons, New York (1994), and Hale & Marham, *THE HARPER COLLINS DICTIONARY OF BIOLOGY*, Harper Perennial, N.Y. (1991) provide one of skill with a general dictionary of many of the terms used with this disclosure.

The disclosure is further defined in the following Examples. It should be understood that the Examples, while indicating certain embodiments, is given by way of illustration only. From the above discussion and the Examples, one skilled in the art can ascertain essential characteristics of this disclosure, and without departing from the spirit and scope thereof, can make various changes and modifications to adapt to various uses and conditions.

Example 1

Sequences of Glucoamylases

The nucleic acid sequence for the FraGA1 gene, and the amino acid sequence of the hypothetical protein encoded by the FraGA1 gene were found in the NCBI database (NCBI Accession No.: NW_012133200.1 (gene) and XP_012178139 (protein)).

The amino acid sequence of the FraGA1 precursor protein is set forth as SEQ ID NO: 1.

```
MLFLLAALGLACSAAAQSTSVSAYIASESPVAKAGVLANIGTEGSLSSGA

YSGVVIASPSTVNPDYLYTWVRDSSLTFQALIDQYVYGEDPTLRSLIDEF

ITAESILQQTTNPSGTVSTGGLGEPKFNINETAFTGPWGRPQRDGPALRS

TAIITYATYLWNSGNTSYVSDSLWPIIELDLNYIATYWNFSTFDLWEEID

SSSFWTTAVQHRALRQGITFANLIGQTSPVSNYETQAGDILCFLQTYWNP

TGNYMTANTGGGRSGKDSNTVLASVHTFDPDAGCDSTTFQPCSDKALSNL

KVYVDSFRSLYAINDGIASDAAVATGRYPEDVYYGGNPWYLCTFAVAEQL
```

-continued

```
YDALIVWSSQGYLEITDLSLAFFQQFDSDVGTGTYDSGSSTYSTLTSAIR

TFADGFVLTNAKYTPTNGSLSEEYTSADGTPISAYDLTWSYASALTVFAA

EAGTTYGSWGAAGLTVPSTCTSGVAVTFEVDYDTEYGENVYITGSVNALE

NWSATNALIMSAADYPTWSITVYLPPSTTIQYKYLTQYNGEVTWEDDPNN

EITTPASGSMTQVDSWH
```

The nucleic acid sequence for the WcoGA1 gene, and the amino acid sequence of the hypothetical protein encoded by the WcoGA1 gene were found in the JGI database (JGI Accession No.: Wolco1150090 (gene) and Wolco1149945 (protein)). The N-terminal signal peptide was predicted by SignalP software version 4.0 (Nordahl Petersen et al. (2011) *Nature Methods*, 8:785-786).

The amino acid sequence of the WcoGA1 precursor protein is set forth as SEQ ID NO: 2.

```
MRLSLASVFALAGGALAQTTSVTSYIASESPIAKAGVLANIGADGSLSSG

AYSGIVIASPSTVNPNYLYTWTRDSSLTFMELINQYIYGEDDTLRTLIDE

FVSAEATLQQVTNPSGTVSTGGLGEPKFNINETAFTGPWGRPQRDGPALR

ATAIMAYATYLYENGNTSYVTDTLWPIIELDLGYVAEWNESTFDLWEEID

SSSFFTTAVQHRALRAGVTFANLIGETSDVSNYQENADDLLCFLQSYWNP

TGSYVTANTGGGRSGKDANTLLASIHTFDPDAGCNATTFQPCSDKALSNH

KVYVDSFRSLYAINDDISSDAAVATGRYPEDVYYNGNPWYLCTLAAAEQL

YDSLIVWKAQGYIEVTSLSLAFFQQFDASVSAGTYDSSSDTYTTLLDAVQ

TYADGFVLMVAQYTPANGSLSEQYAKADGSPTSAYDLTWSFAAALTAFAA

RDGKTYGSWGAADLSSTCSGSTDTVAVTFEVQYDTQYGENLYITGSVSQL

EDWSADDALIMSSADYPTWSITVDLPPSTLIQYKYLTKYNGDVTWEDDPN

NEITTPASGSYTQVDSWH
```

The amino acid sequence of the TeGA precursor protein from *Talaromyces emersonii* is set forth as SEQ ID NO: 3.

```
MASLVAGALCILGLTPAAFARAPVAARATGSLDSFLATETPIALQGVLNN

IGPNGADVAGASAGIVVASPSRSDPNYFYSWTRDAALTAKYLVDAFNRGN

KDLEQTIQQYISAQAKVQTISNPSGDLSTGGLGEPKFNVNETAFTGPWGR

PQRDGPALRATALIAYANYLIDNGEASTADEIIWPIVQNDLSYITQYWNS

STFDLWEEVEGSSFFTTAVQHRALVEGNALATRLNHTCSNCVSQAPQVLC

FLQSYWTGSYVLANFGGSGRSGKDVNSILGSIHTFDPAGGCDDSTFQPCS

ARALANHKVVTDSFRSIYAINSGIAEGSAVAVGRYPEDVYQGGNPWYLAT

AAAAEQLYDAIYQWKKIGSISITDVSLPFFQDIYPSAAVGTYNSGSTTFN

DIISAVQTYGDGYLSIVEKYTPSDGSLTEQFSRTDGTPLSASALTWSYAS

LLTASARRQSVVPASWGESSASSVLAVCSATSATGPYSTATNTVWPSSGS

GSSTTTSSAPCTTPTSVAVTFDEIVSTSYGETIYLAGSIPELGNWSTASA

IPLRADAYTNSNPLWYVTVNLPPGTSFEYKFFKNQTDGTIVWEDDPNRSY

TVPAYCGQTTAILDDSWQ
```

Example 2

Expression of Glucoamylases

DNA sequences encoding full-length FraGA1 and WcoGA1 were synthesized and inserted into the pTTT expression vector (described in published PCT Application WO2011/063308). A DNA sequence encoding the TeGA was synthesized and inserted into the pTrex3gM expression vector (described in U.S. Published Application 2011/0136197 A1).

The nucleotide sequence of the FraGA1 gene used for expression is set forth below as SEQ ID NO: 4.

```
ATGCTCTTCCTCCTCGCTGCTCTGGGCCTCGCTTGTAGCGCTGCTGCCCA

ATCCACTTCCGTCTCCGCTTACATCGCCAGCGAGAGCCCCGTTGCCAAAG

CCGGTGTTCTGGCTAACATTGGCACTGAAGGTAGCCTGAGCTCCGGTGCC

TACTCCGGCGTTGTCATCGCCTCCCCCAGCACCGTCAACCCTGACTACCT

CTATACTTGGGTTCGCGACTCCAGCCTCACTTTCCAAGCCCTGATTGACC

AGTACGTTTACGGCGAGGACCCCACCCTCCGAAGCCTGATCGACGAGTTC

ATTACCGCTGAGTCCATCCTGCAGCAAACTACCAACCCCAGCGGCACCGT

TAGCACCGGCGGTCTGGGCGAGCCCAAGTTCAACATCAATGAGACTGCCT

TTACCGGTCCCTGGGGCCGACCCCAACGCGACGGTCCTGCCCTCCGCAGC

ACTGCCATCATTACTTATGCCACCTACCTGTGGAACTCCGGTAACACCTC

CTACGTTTCCGATTCCCTCTGGCCCATCATCGAACTCGACCTGAATTACA

TTGCTACCTACTGGAATTTCTCCACTTTTGATCTGTGGGAAGAGATTGAC

TCCTCCAGCTTCTGGACCACTGCCGTTCAGCATCGAGCCCTGCGCCAGGG

TATCACCTTCGCTAATCTGATTGGCCAGACCAGCCCTGTCAGCAACTATG

AGACCCAAGCCGGCGATATCCTCTGTTTCCTCCAAACCTATTGGAATCCT

ACCGGCAACTACATGACCGCCAATACTGGCGGTGGTCGAAGCGGCAAGGA

CTCCAACACCGTTCTCGCTTCCGTTCATACCTTCGATCCCGATGCCGGCT

GTGATAGCACTACTTTTCAACCTTGCTCCGACAAGGCCCTGAGCAACCTC

AAGGTCTACGTCGACTCCTTTCGCAGCCTGTACGCCATCAACGACGGTAT

TGCCTCCGACGCTGCCGTCGCCACCGGCCGCTATCCTGAGGACGTCTACT

ACGGCGGTAACCCCTGGTACCTCTGCACCTTTGCTGTCGCCGAACAACTC

TACGACGCCCTCATCGTCTGGAGCAGCCAGGGCTATCTCGAAATCACTGA

CCTCAGCCTGGCCTTCTTCCAGCAGTTTGATTCCGATGTCGGTACTGGCA

CCTACGACAGCGGCTCCAGCACTTACTCCACTCTCACCTCCGCCATCCGA

ACTTTTGCTGATGGCTTCGTTCTGACCAACGCCAAATACACCCCTACCAA

TGGTTCCCTGTCCGAGGAGTACACCAGCGCCGATGGCACTCCTATCTCCG

CCTATGACCTGACCTGGAGCTACGCCTCCGCTCTGACCGTCTTTGCCGCC

GAGGCCGGCACCACTTACGGCTCCTGGGGTGCTGCTGGCCTGACTGTCCC

TAGCACCTGCACTAGCGGCGTCGCTGTTACTTTCGAGGTCGATTACGACA

CCGAGTATGGCGAAAACGTCTATATCACCGGTTCCGTCAATGCCCTGGAA

AATTGGTCCGCCACTAATGCTCTGATTATGTCCGCCGCTGACTATCCCAC

CTGGTCCATCACCGTTTACCTGCCCCCCTCCACCACCATTCAGTATAAGT
```

ATCTCACCCAGTACAACGGCGAAGTCACTTGGGAGGACGACCCTAACAAC

GAGATTACTACCCCTGCTAGCGGTTCCATGACCCAGGTTGACAGCTGGCA

Ctaa

The nucleotide sequence of the WcoGA1 gene used for expression is set forth below as SEQ ID NO: 5.

ATGCGACTGAGCCTGGCCTCCGTTTTTGCTCTCGCCGGTGGTGCCCTCGC

CCAGACCACTAGCGTCACCTCCTACATTGCTAGCGAAAGCCCCATTGCCA

AAGCCGGTGTTCTCGCTAACATTGGCGCTGACGGCTCCCTGAGCTCCGGT

GCTTATTCCGGCATTGTTATCGCCAGCCCCTCCACCGTTAACCCTAACTA

TCTCTATACCTGGACTCGCGACTCCAGCCTGACCTTCATGGAACTGATCA

ACCAGTACATCTACGGCGAGGACGATACTCTGCGAACTCTGATTGATGAG

TTCGTTTCCGCTGAAGCCACCCTCCAACAGGTCACTAATCCTAGCGGCAC

TGTCTCCACTGGTGGCCTCGGCGAGCCCAAGTTCAACATCAACGAGACTG

CTTTTACTGGTCCCTGGGGCCGACCCCAACGCGATGGCCCTGCCCTGCGC

GCTACTGCTATCATGGCCTATGCCACCTACCTGTATGAAAACGGTAATAC

TAGCTATGTTACTGACACCCTCTGGCCCATCATTGAACTCGACCTCGGTT

ACGTCGCCGAATATTGGAACGAAAGCACCTTTGATCTCTGGGAGGAAATC

GACAGCAGCTCCTTTTTCACTACCGCTGTTCAGCACCGCGCTCTCCGCGC

TGGCGTTACCTTCGCCAATCTCATCGGTGAGACCAGCGACGTCAGCAACT

ACCAGGAAAATGCCGACGACCTCCTCTGCTTCCTCCAAAGCTACTGGAAC

CCCACTGGCAGCTACGTCACTGCTAACACTGGCGGTGGTCGAAGCGGCAA

GGACGCCAACACTCTCCTGGCTAGCATCCACACCTTCGATCCCGACGCTG

GCTGCAACGCCACTACCTTTCAACCCTGTTCCGACAAAGCCCTCAGCAAT

CACAAGGTCTACGTTGACTCCTTCCGCAGCCTCTACGCCATCAATGACGA

CATTAGCAGCGATGCCGCTGTCGCTACCGGCCGATACCCTGAGGATGTCT

ACTACAACGGCAACCCCTGGTACCTCTGTACCCTGGCCGCTGCTGAGCAA

CTCTACGACTCCCTCATCGTCTGGAAGGCCCAAGGCTACATCGAAGTCAC

CAGCCTCAGCCTCGCCTTTTTTCAACAGTTCGATGCTTCCGTTAGCGCCG

GTACTTATGATTCCAGCTCCGACACCTACACCACCCTGCTCGACGCCGTT

CAGACCTATGCTGATGGCTTCGTCCTGATGGTCGCTCAGTACACCCCTGC

CAACGGTTCCCTCTCCGAGCAGTACGCCAAGGCCGATGGCAGCCCCACTT

CCGCCTACGACCTGACTTGGTCCTTTGCTGCTGCCCTCACCGCCTTCGCT

GCCCGCGACGGCAAAACCTATGGTAGCTGGGGTGCCGCCGATCTCTCCAG

CACCTGCAGCGGTTCCACCGACACTGTCGCCGTCACTTTCGAGGTCCAGT

ACGACACCCAATATGGTGAAAATCTGTACATTACCGGCAGCGTCTCCCAG

CTCGAGGATTGGAGCGCTGATGATGCTCTCATCATGTCCAGCGCCGACTA

TCCCACCTGGTCCATCACCGTCGATCTGCCCCCTAGCACCCTGATCCAAT

ACAAATACCTCACCAAGTATAACGGCGATGTCACCTGGGAAGACGATCCC

AACAACGAAATTACCACTCCTGCCTCCGGCTCCTATACCCAGGTTGACAG

CTGGCACtaa

The nucleotide sequence of the TeGA gene used for expression is set forth below as SEQ ID NO: 6.

ATGGCCTCCCTGGTTGCTGGTGCTCTGTGCATCCTCGGCCTGACCCCTGC

CGCCTTCGCCCGAGCCCCCGTCGCTGCCCGCGCCACTGGCAGCCTCGACA

GCTTCCTCGCCACCGAGACCCCTATCGCCCTCCAGGGCGTTCTGAACAAC

ATCGGTCCCAACGGCGCTGACGTCGCCGGTGCTAGCGCCGGTATCGTCGT

TGCCAGCCCTAGCCGATCCGACCCCAACTACTTCTACAGCTGGACCCGCG

ACGCCGCTCTCACCGCTAAGTACCTGGTCGACGCCTTCAATCGCGGCAAC

AAAGACCTCGAGCAAACCATCCAGCAGTACATCTCCGCTCAGGCCAAGGT

CCAGACCATTTCCAACCCCAGCGGCGATCTGAGCACTGGCGGCCTGGGCG

AGCCCAAGTTCAACGTCAATGAGACCGCTTTCACTGGCCCCTGGGGCCGA

CCTCAACGCGATGGCCCTGCTCTCCGAGCCACCGCCCTCATCGCCTATGC

TAACTACCTGATCGACAACGGTGAGGCCAGCACTGCCGACGAGATCATCT

GGCCCATCGTCCAAAATGACCTCAGCTACATCACCCAATACTGGAACTCC

AGCACCTTTGACCTGTGGGAGGAGGTCGAGGGCTCCAGCTTCTTCACCAC

TGCTGTTCAGCACCGCGCCCTCGTTGAGGGTAATGCCCTGGCCACCCGAC

TCAATCACACTTGCTCCAACTGCGTCAGCCAGGCCCCCCAGGTCCTCTGC

TTTCTCCAGAGCTACTGGACCGGCAGCTACGTCCTGGCCAACTTTGGTGG

CAGCGGCCGAAGCGGCAAGGACGTCAACAGCATCCTGGGTTCCATCCACA

CCTTCGACCCCGCTGGCGGTTGCGACGACTCCACTTTCCAGCCTTGCAGC

GCTCGCGCTCTCGCCAACCACAAGGTCGTCACCGATTCCTTCCGCTCCAT

CTACGCCATCAATTCCGGCATCGCCGAGGGTAGCGCTGTTGCTGTCGGCC

GCTACCCCGAGGACGTCTACCAAGGCGGCAATCCCTGGTATCTCGCTACT

GCCGCTGCCGCCGAGCAGCTCTATGACGCTATCTATCAGTGGAAAAAGAT

CGGTAGCATCAGCATTACCGACGTCAGCCTCCCCTTCTTCCAGGACATCT

ACCCCTCCGCCGCTGTTGGCACCTACAATTCCGGCTCCACCACCTTCAAC

GACATCATCAGCGCCGTCCAGACTTATGGCGACGGCTACCTGAGCATTGT

CGAGAAGTACACCCCCAGCGATGGCAGCCTCACCGAGCAATTCAGCCGCA

CCGACGGCACCCCCCTGTCCGCTTCCGCCCTCACCTGGAGCTACGCTTCC

CTGCTCACCGCCTCCGCTCGCCGCCAGAGCGTCGTTCCCGCTAGCTGGGG

CGAGAGCAGCGCCAGCTCCGTCCTGGCCGTCTGCTCCGCTACTAGCGCCA

CCGGCCCCTACTCCACTGCCACCAACACCGTTTGGCCTTCCAGCGGCTCC

GGCAGCTCCACTACCACCTCCAGCGCCCCTTGCACCACCCCTACCAGCGT

CGCCGTCACCTTCGACGAGATCGTCAGCACCAGCTACGGCGAGACCATCT

ATCTGGCTGGCAGCATCCCCGAGCTGGGCAATTGGTCCACCGCCAGCGCT

ATTCCTCTGCGCGCTGACGCCTACACTAATAGCAACCCTCTGTGGTATGT

CACCGTTAACCTCCCTCCCGGCACTAGCTTTGAGTATAAGTTTTTCAAGA

ACCAGACCGATGGTACTATTGTCTGGGAGGACGACCCCAACCGATCCTAC

ACCGTCCCCGCCTACTGCGGTCAGACTACCGCTATCCTCGACGATTCCTG

GCAGtaa

The plasmids encoding the FraGA1, WcoGA1 and TeGA enzymes were transformed into a suitable Trichoderma reesei strain using protoplast transformation (Te'o et al., *J. Microbiol. Methods* 51:393-99, 2002). The transformants were selected and fermented by the methods described in WO 2016/138315. Supernatants from these cultures were used to confirm the protein expression by SDS-PAGE analysis and assay for enzyme activity.

FraGA1 was purified via the beta-cyclodextrin coupled Sepharose 6 affinity chromatography, followed by gel filtration chromatography. WcoGA1 was purified via the beta-cyclodextrin coupled Sepharose 6 affinity chromatography followed by hydrophobic interaction chromatography. TeGA was purified via hydrophobic interaction chromatography followed by a beta-cyclodextrin coupled Sepharose 6 affinity chromatography.

Glucoamylase activity assay and SDS-PAGE were performed. The target protein-containing fractions were pooled and concentrated using an Amicon Ultra-15 device with 10 K MWCO. The concentrated solution was then applied onto a Superdex 75 column (GE Healthcare) in buffer A. The target protein eluted from the column in a single peak, which was again pooled and concentrated. The purified sample is above 90% pure and stored in 40% glycerol at −80° C. until usage.

The predicted mature protein sequence of the FraGA1 is set forth below as SEQ ID NO: 7.

QSTSVSAYIASESPVAKAGVLANIGTEGSLSSGAYSGVVIASPSTVNPDY

LYTWVRDSSLTFQALIDQYVYGEDPTLRSLIDEFITAESILQQTTNPSGT

VSTGGLGEPKFNINETAFTGPWGRPQRDGPALRSTAIITYATYLWNSGNT

SYVSDSLWPIIELDLNYIATYWNFSTFDLWEEIDSSSFWTTAVQHRALRQ

GITFANLIGQTSPVSNYETQAGDILCFLQTYWNPTGNYMTANTGGGRSGK

DSNTVLASVHTFDPDAGCDSTTFQPCSDKALSNLKVYVDSFRSLYAINDG

IASDAAVATGRYPEDVYYGGNPWYLCTFAVAEQLYDALIVWSSQGYLEIT

DLSLAFFQQFDSDVGTGTYDSGSSTYSTLTSAIRTFADGFVLTNAKYTPT

NGSLSEEYTSADGTPISAYDLTWSYASALTVFAAEAGTTYGSWGAAGLTV

PSTCTSGVAVTFEVDYDTEYGENVYITGSVNALENWSATNALIMSAADYP

TWSITVYLPPSTTIQYKYLTQYNGEVTWEDDPNNEITTPASGSMTQVDSW

H

The predicted mature protein sequence of the WcoGA1 is set forth below as SEQ ID NO: 8.

QTTSVTSYIASESPIAKAGVLANIGADGSLSSGAYSGIVIASPSTVNPNY

LYTWTRDSSLTFMELINQYIYGEDDTLRTLIDEFVSAEATLQQVTNPSGT

VSTGGLGEPKFNINETAFTGPWGRPQRDGPALRATAIMAYATYLYENGNT

SYVTDTLWPIIELDLGYVAEYWNESTFDLWEEIDSSSFFTTAVQHRALRA

GVTFANLIGETSDVSNYQENADDLLCFLQSYWNPTGSYVTANTGGGRSGK

DANTLLASIHTFDPDAGCNATTFQPCSDKALSNHKVYVDSFRSLYAINDD

ISSDAAVATGRYPEDVYYNGNPWYLCTLAAAEQLYDSLIVWKAQGYIEVT

SLSLAFFQQFDASVSAGTYDSSSDTYTTLLDAVQTYADGFVLMVAQYTPA

NGSLSEQYAKADGSPTSAYDLTWSFAAALTAFAARDGKTYGSWGAADLSS

TCSGSTDTVAVTFEVQYDTQYGENLYITGSVSQLEDWSADDALIMSSADY

PTWSITVDLPPSTLIQYKYLTKYNGDVTWEDDPNNEITTPASGSYTQVDS

WH

The mature protein sequence of the TeGA is set forth below as SEQ ID NO: 9.

ATGSLDSFLATETPIALQGVLNNIGPNGADVAGASAGIVVASPSRSDPNY

FYSWTRDAALTAKYLVDAFNRGNKDLEQTIQQYISAQAKVQTISNPSGDL

STGGLGEPKFNVNETAFTGPWGRPQRDGPALRATALIAYANYLIDNGEAS

TADEIIWPIVQNDLSYITQYWNSSTFDLWEEVEGSSFFTTAVQHRALVEG

NALATRLNHTCSNCVSQAPQVLCFLQSYWTGSYVLANFGGSGRSGKDVNS

ILGSIHTFDPAGGCDDSTFQPCSARALANHKVVTDSFRSIYAINSGIAEG

SAVAVGRYPEDVYQGGNPWYLATAAAAEQLYDAIYQWKKIGSISITDVSL

PFFQDIYPSAAVGTYNSGSTTFNDIISAVQTYGDGYLSIVEKYTPSDGSL

TEQFSRTDGTPLSASALTWSYASLLTASARRQSVVPASWGESSASSVLAV

CSATSATGPYSTATNTVWPSSGSGSSTTTSSAPCTTPTSVAVTFDEIVST

SYGETIYLAGSIPELGNWSTASAIPLRADAYTNSNPLWYVTVNLPPGTSF

EYKFFKNQTDGTIVWEDDPNRSYTVPAYCGQTTAILDDSWQ

Example 3

Stability of Glucoamylases at Low pH and in the Presence of Pepsin

The stability of purified samples of glucoamylases TeGA, FraGA1 and WcoGA1 was analyzed at low pH conditions and in the presence of pepsin. The enzymes were incubated with pepsin (Sigma, Cat. No. P7000) in 50 mM glycine-HCl buffer (pH 2.0) and 1% (w/w) soluble starch prepared in 50 mM MES-NaOH buffer (pH 6.5) was used as the substrate for activity measurements. Glucoamylases and pepsin were first mixed in ratios (w/w) of 1:0 or 1:50, where the glucoamylases were dosed at 100 ppm; and the resulting mixture was subsequently incubated at 40° C. for 30 min. Meanwhile, 100 ppm aliquots of each glucoamylase were incubated in 50 mM MES-NaOH buffer (pH6.5) at 40° C. for 30 min, serving as the untreated controls. To initiate the activity measurement, 10 µL of enzyme dilution (enzyme dose selected in linear range, or water alone as the blank control) was added to 96 well-microtiter plate (MTP, Corning 3641) containing 90 µL of substrate (1% starch) solution. The MTP was subsequently sealed and incubated for 10 min in iEMS (ThermoFisher) at 40° C. and 1150 rpm. The glucoamylase activity was determined as the rate of glucose release that was measured using a coupled glucose oxidase/peroxidase (GOX/HRP) method (*Anal. Biochem.* 105 (1980), 389-397). As shown in Table 2, using glucose release as measure of enzyme activity, the FraGa1, WcoGA1 and TeGA glucoamylases are stable in pH 2.0 buffer, in the presence of absence of exogenous pepsin, unlike the *Trichoderma reesei* wild type glucoamylase (TrGA, pdb file 2VN4_A, SEQ ID NO: 11) that loses all activity at pH 2.0.

TABLE 2

Relative stability of glucoamylases at low pH and with pepsin

| Enzyme | buffer only pH 6.5 | buffer only pH 2.0 | in presence of pepsin pH 2.0 |
|---|---|---|---|
| TeGA | 368 | 372 | 395 |
| FraGA1 | 231 | 215 | 221 |
| WcoGA1 | 235 | 242 | 252 |
| TrGA | 185 | 0 | 0 |

Example 4

Glucogenic Activity of Glucoamylases on Maltodextrin at Low pH

The glucoamylase activity on maltodextrin substrate was measured at pH 3 by analyzing sugar compositions, with enzymes dosed at 5 ppm. Glucoamylases: TeGA, FraGA1, WcoGA1, AnGA (*Aspergillus niger* wild type glucoamylase, accession number XP_001390530.1, SEQ ID NO: 10) and TrGA (*Trichoderma reesei* wild type glucoamylase, pdb file 2VN4_A, SEQ ID NO: 11) were tested on MALTRIN® M040 (Maltodextrin with DE4-7) obtained from Staple Flavour & Fragrance Co. Ltd. The reactions were initiated by adding 10 µL of a 50 ppm sample of the purified glucoamylases to 90 µL of Maltrin substrate (5% w/v) solution in 25 mM Glycine/Na-acetate/HEPES buffer pH 3.0. The incubations were carried out in a PCR incubator at 55° C. for 4 and 22 h, respectively. The reactions were stopped by addition of 50 µL of 0.5 M NaOH and mixing in a shaker for 2 min. The plate was centrifuged to collect the supernatants that were then diluted 20-fold with 5 mM $H_2SO_4$. These samples (10 µL) were analyzed using an Agilent 1200 series HPLC equipped with a refractive index detector, a Phenomenex Rezex-RFQ Fast Fruit column, and a Phenomenex Rezex ROA Organic Acid guard column. A mobile phase of 5 mM $H_2SO_4$, at a flow rate of 1.0 mL/min at 85° C. was applied. Peaks corresponding to DP1, 2, 3 and 3+ were identified. Peak area percentages of DP1 as a fraction of the total DP1, DP2, DP3 and DP3+ were calculated and are shown in Table 3. FraGA1, WcoGA1 and TeGA glucoamylases exhibited higher glucogenic activity than the AnGA and TrGA.

TABLE 3

Percent of total DPs (DP1, 2, 3 and 3+) detected by HPLC separation from maltodextrin digestion by various glucoamylases after 4 and 22 hours.

| Incubation time | Enzyme | DP3+ | DP3 | DP2 | DP1 |
|---|---|---|---|---|---|
| 4 h | AnGA | 43.2 | 1.4 | 4.6 | 50.8 |
|  | TrGA | 55.4 | 2.8 | 2.4 | 39.3 |
|  | TeGA | 22.2 | 0.4 | 0 | 77.4 |
|  | FraGA1 | 18.2 | 0.6 | 5 | 76.3 |
|  | WcoGA1 | 15 | 0.2 | 2.6 | 82.2 |
| 22 h | AnGA | 22.6 | 0 | 1 | 76.4 |
|  | TrGA | 43.5 | 2.4 | 3.5 | 50.6 |
|  | TeGA | 10.9 | 0.2 | 0.6 | 88.3 |
|  | FraGA1 | 12.6 | 0.3 | 2.6 | 84.5 |
|  | WcoGA1 | 9 | 0.4 | 0.5 | 90.1 |

Example 5

Glucogenic Activity on Starch Liquefact of Glucoamylases Measured at Low pH The glucoamylases FraGA1, WcoGA1, TrGA and AnGA were evaluated on starch liquefact to measure their glucogenic activity and DP3 and DP3+ hydrolysis at low pH. The pH of corn starch liquefact (32% ds, alpha-amylase-pretreated) was adjusted to pH 3.0. The above substrate (10 g) and the glucoamylases (dosed at 0.25 mg/gds) were incubated at 32° C. and 55° C., respectively. The reaction mixtures (100 µL) were incubated for 17, 24, 41, 48, 63, or 72 h, at which time the reactions were quenched by heating at 100° C. for 15 min. Following centrifugation, supernatants were transferred to new containers and diluted 400-fold in 5 mM $H_2SO_4$ for HPLC analysis using the same conditions as described above in EXAMPLE 4. The values reported in Table 4 are the peak area percentages of each DPn as a fraction of the total DP1, DP2, DP3, and DP3+. The results in Table 4 show that FraGA1 and WcoGA1 exhibited higher glucogenic activity and faster DP3+ hydrolysis than TrGA and AnGA when dosed at equal protein amount (0.25 mg/gds) and incubated at 32° C. at pH 3. When the incubation temperature was increased to 55° C., WcoGA1 and FraGA1 hydrolyzed DP3+ very efficiently, with only 3%, 4% and 5% DP3+ remaining after a 17 h incubation, respectively, while 18% and 13% remained in TrGA and AnGA reactions, respectively.

FraGA1, WcoGA1, TrGA and AnGA were further evaluated for activity towards starch liquefact at pH 2.0. The incubation procedure was the same as described above except that the enzymes were dosed at 0.2 mg/gds and incubations were carried out at pH 2.0. Samples were collected at 4, 21, 29, 45, 53, and 70 h. At pH 2, FraGA1 and WcoGA1 greatly outperformed TrGA and AnGA on DP3+ hydrolysis rate and final DP1 conversion as shown in Table 5. FraGA1 and WcoGA1 produced ≥90% and ≥72% DP1 after a 70 h incubation at 32° C. and 55° C., respectively, while TrGA yielded only 54% and 3%. These results indicate that FraGA1 and WcoGA1 have high potential in saccharification and simultaneous saccharification and fermentation (SSF) process, with significant activity at pH 2.0-3.0 and 30-55° C.

TABLE 4

Relative hydrolysis at pH 3 by glucoamylases tested at 32° C. or 55° C. using starch liquefact as a substrate.

| Enzyme | Incubation temp. (° C.) | Time (h) | DP3+% | DP3% | DP2% | DP1% |
|---|---|---|---|---|---|---|
| AnGA | 32 | 17 | 35.9 | 0.6 | 7.3 | 56.1 |
|  |  | 24 | 27.2 | 0.3 | 2.9 | 69.5 |
|  |  | 41 | 19.2 | 0.5 | 1.0 | 79.3 |
|  |  | 48 | 16.9 | 0.5 | 1.1 | 81.4 |
|  |  | 63 | 14.5 | 0.0 | 1.3 | 84.2 |
|  |  | 72 | 12.7 | 0.4 | 1.3 | 85.6 |
| TrGA | 32 | 17 | 36.9 | 1.2 | 6.1 | 55.8 |
|  |  | 24 | 24.7 | 0.6 | 3.9 | 70.8 |
|  |  | 41 | 20.9 | 0.6 | 1.5 | 77.1 |
|  |  | 48 | 18.2 | 0.5 | 1.5 | 79.8 |
|  |  | 63 | 15.2 | 0.2 | 1.6 | 82.9 |
|  |  | 72 | 14.3 | 0.4 | 1.7 | 83.6 |
| FraGA1 | 32 | 17 | 12.5 | 0.5 | 2.1 | 84.8 |
|  |  | 24 | 6.5 | 0.4 | 2.5 | 90.6 |
|  |  | 41 | 4.1 | 0.4 | 4.1 | 91.4 |
|  |  | 48 | 4.6 | 0.0 | 4.6 | 90.8 |
|  |  | 63 | 3.2 | 0.0 | 6.0 | 90.8 |
|  |  | 72 | 3.7 | 0.6 | 6.3 | 89.4 |

TABLE 4-continued

Relative hydrolysis at pH 3 by glucoamylases tested at 32° C. or 55° C. using starch liquefact as a substrate.

| Enzyme | Incubation temp. (° C.) | Time (h) | DP3+% | DP3% | DP2% | DP1% |
|---|---|---|---|---|---|---|
| WcoGA1 | 32 | 17 | 20.3 | 0.7 | 1.9 | 77.2 |
|  |  | 24 | 13.2 | 0.5 | 1.7 | 84.6 |
|  |  | 41 | 8.0 | 0.2 | 2.3 | 89.5 |
|  |  | 48 | 7.5 | 0.4 | 2.8 | 89.4 |
|  |  | 63 | 4.9 | 0.2 | 3.4 | 91.4 |
|  |  | 72 | 4.6 | 0.0 | 3.6 | 91.8 |
| AnGA | 55 | 17 | 13.0 | 0.4 | 1.7 | 84.9 |
|  |  | 24 | 9.1 | 0.3 | 2.0 | 88.6 |
|  |  | 41 | 5.9 | 0.3 | 2.7 | 91.1 |
|  |  | 48 | 5.5 | 0.2 | 2.8 | 91.5 |
|  |  | 63 | 4.9 | 0.0 | 3.2 | 91.9 |
|  |  | 72 | 4.0 | 0.0 | 3.6 | 92.4 |
| TrGA | 55 | 17 | 18.1 | 0.6 | 2.6 | 78.7 |
|  |  | 24 | 14.2 | 0.5 | 2.3 | 83.1 |
|  |  | 41 | 9.7 | 0.4 | 2.7 | 87.3 |
|  |  | 48 | 8.9 | 0.4 | 2.7 | 88.0 |
|  |  | 63 | 7.2 | 0.0 | 3.0 | 89.8 |
|  |  | 72 | 6.7 | 0.2 | 3.1 | 89.9 |
| FraGA1 | 55 | 17 | 3.9 | 0.6 | 6.2 | 89.2 |
|  |  | 24 | 1.6 | 0.8 | 8.2 | 89.4 |
|  |  | 41 | 1.6 | 1.3 | 10.9 | 86.2 |
|  |  | 48 | 1.9 | 1.5 | 11.6 | 85.0 |
|  |  | 63 | 2.0 | 0.0 | 12.8 | 85.2 |
|  |  | 72 | 1.9 | 1.7 | 12.9 | 83.5 |
| WcoGA1 | 55 | 17 | 3.2 | 0.5 | 4.5 | 91.9 |
|  |  | 24 | 2.1 | 0.6 | 5.9 | 91.4 |
|  |  | 41 | 2.0 | 0.9 | 8.2 | 88.8 |
|  |  | 48 | 2.2 | 1.1 | 9.1 | 87.6 |
|  |  | 63 | 2.1 | 0.0 | 10.7 | 87.2 |
|  |  | 72 | 1.9 | 1.5 | 10.9 | 85.8 |

TABLE 5

Relative hydrolysis at pH 2 by glucoamylases tested at 32° C. or 55° C. using starch liquefact as a substrate.

| Enzyme | Incubation temp. (° C.) | Time (h) | DP3+% | DP3% | DP2% | DP1% |
|---|---|---|---|---|---|---|
| AnGA | 32 | 4 | 75.6 | 8.3 | 4.5 | 11.5 |
|  |  | 21 | 35.8 | 2.2 | 12.5 | 49.5 |
|  |  | 29 | 33.1 | 0.0 | 9.9 | 57.0 |
|  |  | 45 | 26.1 | 0.0 | 3.6 | 70.3 |
|  |  | 53 | 23.8 | 0.2 | 2.0 | 74.0 |
|  |  | 70 | 21.2 | 0.3 | 1.2 | 77.3 |
| TrGA | 32 | 4 | 77.7 | 7.7 | 4.5 | 10.1 |
|  |  | 21 | 48.5 | 6.2 | 10.1 | 35.2 |
|  |  | 29 | 44.1 | 4.2 | 11.1 | 40.6 |
|  |  | 45 | 36.6 | 1.9 | 12.2 | 49.3 |
|  |  | 53 | 35.3 | 1.3 | 12.0 | 51.5 |
|  |  | 70 | 33.5 | 0.9 | 11.6 | 54.0 |
| FraGA1 | 32 | 4 | 52.2 | 8.0 | 7.7 | 32.2 |
|  |  | 21 | 17.3 | 0.6 | 3.8 | 78.3 |
|  |  | 29 | 13.4 | 0.6 | 2.4 | 83.5 |
|  |  | 45 | 8.1 | 0.0 | 2.4 | 89.5 |
|  |  | 53 | 6.5 | 0.0 | 2.6 | 90.9 |
|  |  | 70 | 3.9 | 0.2 | 3.3 | 92.6 |
| WcoGA1 | 32 | 4 | 53.9 | 7.8 | 8.5 | 29.8 |
|  |  | 21 | 20.1 | 0.6 | 3.1 | 76.2 |
|  |  | 29 | 16.1 | 0.6 | 2.0 | 81.2 |
|  |  | 45 | 11.7 | 0.3 | 2.0 | 86.1 |
|  |  | 53 | 10.5 | 0.2 | 2.2 | 87.1 |
|  |  | 70 | 7.8 | 0.0 | 2.6 | 89.5 |
| AnGA | 55 | 4 | 44.5 | 5.2 | 10.5 | 39.8 |
|  |  | 21 | 32.4 | 1.4 | 11.6 | 54.6 |
|  |  | 29 | 34.1 | 1.3 | 11.4 | 53.2 |
|  |  | 45 | 31.5 | 1.3 | 11.6 | 55.6 |
|  |  | 53 | 31.9 | 1.3 | 11.4 | 55.4 |
|  |  | 70 | 32.9 | 1.3 | 11.4 | 54.4 |

TABLE 5-continued

Relative hydrolysis at pH 2 by glucoamylases tested at 32° C. or 55° C. using starch liquefact as a substrate.

| Enzyme | Incubation temp. (° C.) | Time (h) | DP3+% | DP3% | DP2% | DP1% |
|---|---|---|---|---|---|---|
| TrGA | 55 | 4 | 87.3 | 6.1 | 3.6 | 3.0 |
|  |  | 21 | 87.2 | 5.9 | 3.8 | 3.2 |
|  |  | 29 | 87.2 | 6.0 | 3.7 | 3.1 |
|  |  | 45 | 86.6 | 6.0 | 3.9 | 3.4 |
|  |  | 53 | 86.9 | 6.1 | 3.8 | 3.2 |
|  |  | 70 | 87.1 | 6.0 | 3.7 | 3.2 |
| FraGA1 | 55 | 4 | 25.0 | 0.7 | 10.0 | 64.3 |
|  |  | 21 | 18.0 | 0.6 | 4.9 | 76.5 |
|  |  | 29 | 16.7 | 0.6 | 4.6 | 78.0 |
|  |  | 45 | 16.4 | 0.6 | 4.4 | 78.6 |
|  |  | 53 | 17.1 | 0.7 | 4.4 | 77.9 |
|  |  | 70 | 16.0 | 0.7 | 4.3 | 79.0 |
| WcoGA1 | 55 | 4 | 26.2 | 0.6 | 9.1 | 64.1 |
|  |  | 21 | 22.7 | 0.7 | 5.6 | 71.0 |
|  |  | 29 | 21.5 | 0.6 | 5.6 | 72.3 |
|  |  | 45 | 21.0 | 0.6 | 5.6 | 72.8 |
|  |  | 53 | 22.5 | 0.6 | 5.6 | 71.3 |
|  |  | 70 | 21.5 | 0.6 | 5.6 | 72.2 |

Example 6

Evaluation of Glucoamylases on Saccharification at pH 3.5 and 4.5

The saccharification performance of FraGA1 and WcoGA1 and AnGA was evaluated at traditional pH 4.5 condition, and a lower pH, 3.5. DP1 production was measured by analyzing sugar composition after treatment with equal enzyme dosage. The incubations of glucoamylases (dosed at 50 μg/gds) and alpha-amylase-pretreated corn starch liquefact (32% ds) were performed at 60° C., pH 3.5 and 4.5, and samples were collected at 24, 48, and 72 h. All incubations were quenched by heating at 100° C. for 15 min. Following centrifugation, supernatants from each sample were transferred to new tubes and diluted 400-fold in 5 mM $H_2SO_4$ for HPLC analysis. HPLC separation was performed using an Agilent 1200 series HPLC system with a Fast fruit column (100 mm×7.8 mm) at 80° C. with an isocratic gradient of 5 mM $H_2SO_4$ at a flow rate of 1.0 mL/min. The oligosaccharide products were detected using a refractive index detector. The glucogenic activities of the samples are summarized in Table 6. The DP1 production by FraGA1 and WcoGA1 at pH 3.5 after 48 h incubation was comparable to results using AnGA at pH 4.5 after a 72 h incubation.

TABLE 6

Sugar composition analysis of corn starch liquefact treated with FraGA1 WcoGA1 or AnGA at 60° C., at pH 3.5 or 4.5 for 24, 48 or 72 h.

| pH | Time | Sample | DP3+% | DP3% | DP2% | DP1% |
|---|---|---|---|---|---|---|
| 3.5 | 24 h | AnGA | 27.7 | 2.1 | 7.7 | 62.5 |
|  |  | FraGA1 | 10.0 | 0.8 | 3.5 | 85.7 |
|  |  | WcoGA1 | 13.6 | 0.8 | 3.9 | 81.7 |
|  | 48 h | AnGA | 15.7 | 0.8 | 1.5 | 82.0 |
|  |  | FraGA1 | 4.0 | 0.5 | 4.2 | 91.4 |
|  |  | WcoGA1 | 5.2 | 0.4 | 3.6 | 90.8 |
|  | 72 h | AnGA | 13.8 | 1.1 | 2.8 | 82.3 |
|  |  | FraGA1 | 2.5 | 0.7 | 5.4 | 91.3 |
|  |  | WcoGA1 | 3.0 | 0.7 | 5.0 | 91.3 |
| 4.5 | 24 h | AnGA | 19.5 | 2.2 | 11.0 | 67.3 |
|  |  | FraGA1 | 11.8 | 1.2 | 4.7 | 82.3 |
|  |  | WcoGA1 | 11.2 | 1.1 | 3.8 | 84.0 |

TABLE 6-continued

Sugar composition analysis of corn starch liquefact treated with FraGA1 WcoGA1 or AnGA at 60° C., at pH 3.5 or 4.5 for 24, 48 or 72 h.

| pH | Time | Sample | DP3+% | DP3% | DP2% | DP1% |
|---|---|---|---|---|---|---|
|  | 48 h | AnGA | 8.5 | 1.4 | 1.7 | 88.4 |
|  |  | FraGA1 | 5.6 | 0.8 | 3.7 | 90.0 |
|  |  | WcoGA1 | 4.9 | 0.7 | 3.4 | 91.0 |
|  | 72 h | AnGA | 5.0 | 1.3 | 2.2 | 91.5 |
|  |  | FraGA1 | 3.7 | 0.9 | 4.7 | 90.6 |
|  |  | WcoGA1 | 2.5 | 0.8 | 4.6 | 92.1 |

Example 7

Stability of FraGA1 and WcoGA1 Under Ruminant Digestion Conditions

The stability of FraGA1 and WcoGA1 enzymes was measured at pH 2.2, 5.6 and 6.5 under ruminant digestion conditions in vitro as described below.

Assay Conditions at pH 5.6:

The reaction mixture contained 1 mL of rumen fluid collected from local dairy cows (Foulum, Denmark), having a measured pH of 5.6 and 20 μL of glucoamylase (the protein concentration of FraGA1 was 5 mg/mL and the protein concentration of WcoGA1 was 6.5 mg/mL). The reaction mixtures were maintained at 40° C. for 10 h with shaking at 100 rpm. A reaction mixture kept at 5° C. served as control; for blank, no enzymes were added. Each enzyme treatment or blank was performed in triplicate. At the end of the incubation period, 0.5 mL of 10% (w/w) corn starch (Sigma, S-4126) was added and the samples were further incubated for 140 min at 40° C. and with shaking at 240 rpm. The percent (%) residual activity was calculated as follows: activity after incubation with enzyme at 40° C. minus the blank, divided by the activity after incubation with enzyme at 5° C. minus the blank, multiplied by 100.

Assay Conditions at pH 6.5:

The conditions were the same as described above of pH 5.6, except that pH was adjusted to pH 6.5 and DTT was added to 20 mM.

Assay Conditions at pH 2.2:

Rumen fluid that was frozen after collection was then thawed and centrifuged prior to use. The supernatant was discarded and the precipitate was suspended in purified water at a ratio (precipitate vs. water) of 1:3. The pH of suspended slurry was adjusted to pH 2.2. Aliquots of 0.6 mL were added to 2 mL tubes containing 0.4 mL pepsin (2500 U pepsin/mL, Sigma P7000) in 60 mM glycine-HCl (pH2.0) and 20 μL each of glucoamylases (the protein concentration of FraGA1 was 5 mg/mL and the protein concentration of WcoGA1 was 6.5 mg/mL). The reaction mixtures were incubated at 40° C. for 3 h with shaking at 100 rpm. At the end of the incubation, 0.5 mL of 15% (w/w) corn starch (Sigma, S-4126) suspended in 250 mM MES pH 6.5 was added and samples were incubated for 3 h at 40° C. The percent (%) residual activity was calculated as follows: activity after incubation with enzyme at 40° C. minus the blank, divided by the activity without pre-incubation (control) minus blank, multiplied by 100.

At the end of each reaction, the assay tubes were centrifuged and supernatants were transferred to PCR plates and heat-treated at 95° C. for 5 min. Samples in the heat-treated PCR tubes were run over 96 well filter plates, and 10 uL aliquots of each filtrate were used to quantify glucose content by HPLC using a BioRad carbohydrate column (Aminex HPX-87N) and water as the eluent, at 75° C. Glucose content was used as a measure of glucoamylase activity on starch substrate. As shown on Table 7, it was observed that the glucoamylases FraGA1 and WcoGA1 retained 60-70% residual activity after incubations at 40° C. at pH5.6 and at pH 6.5 after 10 h. It was also observed that following incubation in the presence of swine pepsin at pH 2.2 and 40° C. for 3 h, these two glucoamylases retained approximately 90% activity.

TABLE 7

Residual activity (percent remaining) of FraGA1 and WcoGA1 glucoamylases under ruminant digestion conditions measured on corn starch.

| Glucoamylases | 40° C. and pH 5.6, 10 h | 40° C. and pH 6.5 10 h | 40° C. and pH 2.2, 3 h in the presence of pepsin |
|---|---|---|---|
| FraGA1 | 64% | 73% | 94% |
| WcoGA1 | 68% | 68% | 89% |

Example 8

Stability and Activity of FraGA1 and WcoGA1 Under Small Instestinal Digestion Conditions In order to simulate small intestinal digestion conditions, one portion rumen fluid was mixed with two portions of artificial rumen fluid according to protocol described by Menke and Steingass (Liu, J. X., A. Susenbeth, and K. H. Südekum. 2002. In vitro gas production measurements to evaluate interactions between untreated and chemically treated rice straws, grass hay, and mulberry leaves. Journal of Animal Science 80:517-524). Corn flour was added to a final concentration of 10% (w/w) and adjusted to pH 6.5. One mL of this mixture was mixed with 50 μL of porcine pancreatin (Sigma, P7545, 50 mg/mL pancreatin stock solution) and 15 μL of a glucoamylase sample (0.08 mg FraGA1 or 0.10 mg WcoGA). For Blank sample, neither pancreatin nor the glucoamylase was added. The reactions were carried out 40° C. for 3 h with shaking at 240 rpm. The reaction mixtures were then centrifuged at 4000 rpm for 10 min and 150 μL of supernatant were transferred to a PCR plate and heated at 95° C. for 5 min. 50 μL aliquots were transferred to a 0.45 μm filter plate and 90 μL water was added and the plate was centrifuged at 4000 rpm for 15 min. The filtrate was analyzed for glucose (G1), maltose (G2) and maltotriose (G3) content by HPLC as described in Example 7. Each treatment or blank reaction was performed in triplicate and the average of the values is reported on Table 8. Std. dev means standard deviation.

TABLE 8

Release of glucose (G1), maltose (G2) and maltotriose (G3) from corn flour by glucoamylase FraGA1 and WcoGA1 and their mixture with porcine pancreatin.

| Treatment | G1 peak area average | Std. dev | G2 peak area average | Std. dev | G3 peak area average | Std. dev |
|---|---|---|---|---|---|---|
| Blank (no enzyme) | 5.7 | 0.38 | 9.4 | 0.48 | 2.2 | 0.17 |
| Porcine pancreatin | 10.8 | 1.47 | 30.1 | 5.68 | 11.7 | 3.05 |
| FraGA1 | 12.2 | 0.10 | 6.2 | 0.08 | 0 | 0 |
| WcoGA1 | 17.7 | 1.72 | 2.9 | 0.39 | 0.3 | 0.04 |

TABLE 8-continued

Release of glucose (G1), maltose (G2) and maltotriose
(G3) from corn flour by glucoamylase FraGA1 and
WcoGA1 and their mixture with porcine pancreatin.

| Treatment | G1 peak area average | Std. dev | G2 peak area average | Std. dev | G3 peak area average | Std. dev |
|---|---|---|---|---|---|---|
| FraGA1 + pancreatin | 24.7 | 1.58 | 39.4 | 1.08 | 4.0 | 1.91 |
| WcoGA1 + pancreatin | 36.1 | 0.98 | 30.4 | 0.25 | 3.4 | 0.49 |

As shown on Table 8, porcine pancreatin releases glucose, maltose and maltotriose from the corn flour. Both FraGA1 and WcoGA1 enzymes release glucose from raw starch in the corn flour. WcoGA1 was also capable of reducing the level of maltose under the experimental conditions. A combination of the glucoamylases with the pancreatin generates glucose, maltose and reduces the maltotriose. These results suggest that the glucoamylases can work together with the alpha-amylase present in pancreatin even in the presence of digestive proteases present in porcine pancreatin (as reported by the manufacturer). In vivo, the glucose generated could be absorbed directly by the animal, while the maltose formed could be converted to glucose by the brush border bound maltase-glucoamylase on the epithelial cells of the small intestine. The corn flour made from corn dent had the following composition: 88.2% dry matter, 9.3% crude protein, 2.0% acid detergent fiber, 6.6% neutral detergent fiber treated with amylase, 78.5% non-fibrous carbohydrates, and 89.0% total digestible nutrients, and was ground to less than 200 μm.

Example 9

FraGA1 to Increase Dry Matter Digestion and Gas Production in the Ruminal Fermentation on Corn The effects of FraGA1 were evaluated on dry matter digestibility (DMD), gas production, starch digestibility and pH in an in vitro batch fermentation system using dent corn as substrate (4 mm ground). The efficacy of FraGA1 was evaluated at three doses (0, 0.25, 0.5, and 0.75 mg/g of substrate as fed basis) in three separate runs with four replications per enzyme-dose combination in each run. The effectiveness of each enzyme was determined on the rumen fermentation pattern after incubation of buffered rumen contents with substrate in a fermentation setup described earlier (Adesogan, A. T., Krueger, N. K., and Kim, S. C. 2005. Anim. Feed Sci. Technol. 123: 211-223; Krueger, N. A., and A. T. Adesogan. 2008. Anim. Feed Sci. Tech. 145: 84-94; Goering, H. K. and P. J. Van Soest. 1970. Agric. Handbook No. 379. ARS USDA, Washington, D.C., pp. 20). The composition of the dent corn used in this in vitro batch fermentation system was given in Example 8. Samples of 0.5 g of dent corn, ground to 4 mm, were weighed into 4 replicate F57 filter bags (ANKOM Technology, Macedon, N.Y.). The enzyme FraGA1 was prepared in 0.1 M citrate-phosphate buffer (pH 6.0) and added onto the ground dent corn in the filter bags at 0, 0.25, 0.5 and 0.75 mg enzyme protein per gram substrate. The filter bags were then sealed with an Uline Tabletop Poly Bag Sealer (Impulse® type AIE-200) and immediately placed in 160 mL serum bottles containing buffered rumen fluid (52 mL). Blank bottles containing only a filter bag, as well as controls containing only ground dent corn with no enzyme beside the buffered rumen fluid were also included. The bottles were then closed with rubber stoppers and sealed with aluminum seals. They were incubated for 7 h at 39° C. in a forced-air incubator. At the end of incubation, the filter bags containing the residues of the dent corn were oven-dried at 60° C. for 48 h and weighed in order to quantify DMD. The gas pressure within the bottles was measured with a pressure transducer and posteriorly converted to gas volume after the 7 h incubation. The following formula was used for the conversion of gas pressure to gas volume: Gas volume (mL)=(Gas pressure (psi)*4.8843)+3.1296. The equation was formulated based on the experimental conditions.

Preparation of the buffered rumen fluid was as follows: ruminal fluid was aspirated from three lactating, ruminally-cannulated Holstein dairy cows 2 to 3 h after consuming total mixed ration (TMR). The TMR ingredient composition fed to the ruminally-cannulated dairy cows based on dry matter consisted of: 38.2% corn silage, 27.3% ground shelled corn, 14.5% soybean meal with 44% crude protein, 9.1% citrus pulp, 4.5% Feedlot premix, 4.0% alfalfa hay mid bloom, 1.8% energy booster (MS Specialty Nutrition, Dundee, Ill.), and 0.5% Novasil (BASF, Germany). The rumen fluid collected was filtered through four layers of cheesecloth prior to mixing with pre-warmed artificial saliva (39° C.). The composition of the artificial saliva included a micromineral solution of $CaCl_2.2H_2O$, $MnCl_2.4H_2O$, $COCl_2.6H_2O$, $FeCl_2.6H_2O$; a macromineral solution of $Na_2HPO_4.12H_2O$, $KH_2PO_4$, $MgSO_4.7H_2O$; a buffer solution of $(NH_4)_2HCO_3$ and $NaHCO_3$; a trypticase peptone solution (tryptone, Sigma-Aldrich, St Louise, Mo., USA); oxidation-reduction indicator resazurin and a reducing solution containing cysteine HCl, 1 M NaOH, $Na_2S.9H_2O$ and distilled water (Goering, H. K. and P. J. Van Soest. 1970. Agric. Handbook No. 379. ARS USDA, Washington, D.C., pp. 20). The volume ratio between the rumen fluid and the artificial saliva was 1:2.

Statistical analysis: For all the experiments in Example 9, the data collected were analyzed using the GLIMMIX procedure of SAS (version 9.1; SAS Institute, Cary, N.C.). Experiments were designed as completely randomized block design where each run was considered a block. Dose was used as fixed effect in the model when enzymes were tested at different doses. Response variable included in-vitro DMD and gas production. Run was considered a random factor. Fixed effects of the model included sampling time for the fermentation parameters measured at different times post-incubation. The UNIVARIATE procedure of SAS was used to test the residuals for outliers and normality before the final analyses were performed. Treatment effects were declared significant at $P<0.05$ while any trends were defined at $0.05 \le P \le 0.10$.

Results: The results shown in Table 9 below indicate that under in vitro rumen fermentation conditions described herein, the glucoamylase FraGA1 increased DMD and gas production in a dose dependent manner. There is a tendency of increased starch digestibility at dose of 0, 0.25 and 0.5 mg enzyme protein per gram ground dent corn. The pH was quite constant irrespective of the enzyme dosages.

TABLE 9

In-vitro responses to exogenous FraGA1 enzyme tested at various doses on dry matter digestibility, gas production, pH levels, and starch digestibility using dent corn grain as substrate.

| Variables | mg/mL FraGA1 | | | | SE | P-value |
|---|---|---|---|---|---|---|
| | 0 | 0.25 | 0.50 | 0.75 | | |
| DMD, % | 13.9$^b$ | 17.3$^a$ | 18.1$^a$ | 18.5$^a$ | 0.62 | <0.01 |
| Gas production, mL | 8.77$^b$ | 12.1$^a$ | 11.8$^a$ | 12.7$^a$ | 0.52 | <0.01 |
| pH | 6.67 | 6.79 | 7.02 | 6.64 | 0.14 | 0.21 |
| Starch digestibility, % | 21.4 | 23.7 | 27.0 | 23.7 | 2.27 | 0.39 |

$^{a-b}$Means within a row with different superscripts differ (P < 0.05).

Example 10

Protein Sequence Comparisons

Related proteins were identified by a BLAST search (Altschul et al., *Nucleic Acids Res.*, 25:3389-402, 1997) using the predicted mature amino acid sequences for FraGA1 (SEQ ID NO: 7), WcoGA1 (SEQ ID NO: 8) and TeGA (SEQ ID NO: 9) against NCBI and Genome Quest Patent databases with search parameters set to default values and a subset are shown on Tables 10A and 10B (FraGA1), Tables 11A and 11B (WcoGA1) and Tables 12A and 12B (TeGA) respectively. Percent identity (PID) for both search sets is defined as the number of identical residues divided by the number of aligned residues in the pairwise alignment. Value labeled "Sequence length" on tables corresponds to the length (in amino acids) for the proteins referenced with the listed Accession numbers, while "Aligned length" refers to sequence used for alignment and PID calculation.

TABLE 10A

List of sequences with percent identity to FraGA1 predicted mature protein identified from the NCBI non-redundant protein database

| Accession # | PID | Organism | Sequence Length | Alignment Length |
|---|---|---|---|---|
| XP_012178139 | 100% | *Fibroporia radiculosa* | 567 | 551 |
| XP_002475369.1 | 80% | *Postia placenta* Mad-698-R | 569 | 552 |
| PCH39892.1 | 80% | *Wolfiporia cocos* MD-104 SS10 | 569 | 554 |
| BAE47183.1 | 77% | *Fomitopsis palustris* | 570 | 552 |
| KZT67263.1 | 77% | *Daedalea quercina* L-15889 | 571 | 553 |
| EPS97511.1 | 76% | *Fomitopsis pinicola* FP-58527 SSI | 570 | 554 |
| OCH90932.1 | 74% | *Obba rivulosa* | 573 | 556 |

TABLE 10B

List of sequences with percent identity to FraGA1 predicted mature protein identified from Genome Quest database

| GQ Identifier | PID | Organism | Length | Align. length |
|---|---|---|---|---|
| US20090325240-1847 | 76.7 | *Fomitopsis palustris* | 570 | 554 |
| KR834708- AUZ02575 | 74.9 | *Fomitopsis palustris* | 550 | 534 |
| WO2014177541 (multiple sequences) | 72.8 | *Trametes cinpulata* synthetic | 556 | 555 |
| WO2016196202-0012 | 72.6 | *Pyrococcus furiosus* | 556 | 555 |
| US20170314003-0002 | 72.1 | *Nigrofomes* sp. | 575 | 556 |

TABLE 10B-continued

List of sequences with percent identity to FraGA1 predicted mature protein identified from Genome Quest database

| GQ Identifier | PID | Organism | Length | Align. length |
|---|---|---|---|---|
| US20080318284-0005 | 72.0 | *Trametes cingulata* | 561 | 560 |
| WO2015065871-BBZ68582 | 71.6 | *Trametes cingulata* | 561 | 560 |

TABLE 11A

List of sequences with percent identity to WcoGA1 predicted mature protein identified from the NCBI non-redundant protein database

| Accession # | PID | Organism | Sequence Length | Alignment Length |
|---|---|---|---|---|
| PCH39892.1 | 100% | *Wolfiporia cocos* MD-104 SS10 | 569 | 552 |
| XP_002475369.1 | 82% | *Postia placenta* Mad-698-R | 569 | 551 |
| XP_012178139.1 | 80% | *Fibroporia radiculosa* | 567 | 554 |
| BAE47183.1 | 80% | *Fomitopsis palustris* | 570 | 552 |
| EPS97511.1 | 79% | *Fomitopsis pinicola* FP-58527 SS1 | 570 | 552 |
| KZT67263.1 | 79% | *Daedalea quercina* L-15889 | 571 | 553 |
| KZT09226.1 | 76% | *Laetiporus sulphureus* 93-53 | 570 | 554 |
| OCH90932.1 | 71% | *Obba rivulosa* | 573 | 556 |

TABLE 11B

List of sequences with percent identity to WcoGA1 predicted mature protein identified from Genome Quest database

| GQ Identifier | PID | Organism | Length | Align. length |
|---|---|---|---|---|
| US20090325240-1847 | 80.1% | *Fomitopsis palustris* | 570 | 554 |
| KR834708-AUZ02575 | 78.0 | *Fomitopsis palustris* | 550 | 532 |
| WO2014177541 (multiple sequences) | 72.2 | *Trametes cingulata* synthetic | 556 | 555 |
| WO2016196202-0012 | 72.1 | *Pyrococcus furiosus* | 556 | 555 |
| US20080318284-0005 | 71.4 | *Trametes cingulata* | 561 | 560 |
| US20170314003-0002 | 71.0 | *Nigrofomes* sp | 575 | 556 |

TABLE 12A

List of sequences with percent identity to TeGA predicted mature protein identified from the NCBI non-redundant protein database

| Accession # | PID | Organism | Sequence Length | Alignment Length |
|---|---|---|---|---|
| CAC28076.1 | 99% | *Rasamsonia emersonii* | 618 | 590 |
| XP_013329152.1 | 93% | *Rasamsonia emersonii* CBS 393.64 | 617 | 590 |
| GAD95639.1 | 75% | *Byssochlamys spectabilis* No. 5 | 622 | 591 |
| KUL85250.1 | 71% | *Talaromyces verruculosus* | 616 | 595 |
| GAM40728.1 | 70% | *Talaromyces cellulolyticus* | 616 | 595 |

TABLE 12B

List of sequences with percent identity to TeGA predicted
mature protein identified from Genome Quest database

| GQ Identifier | PID | Organism | Length | Align. length |
|---|---|---|---|---|
| W02015065871-0007 | 100 | *Rasamsonia emersonii* | 591 | 591 |
| KR1020010032489-0007 | 99.83 | *Talaromyces emersonii* | 591 | 591 |
| W02014060474-0002 | 99.66 | *Talaromyces emersonii* | 593 | 593 |
| EP1951867-0001 | 99.49 | *Rasamsonia emersonii* | 591 | 591 |
| CN101310016-0001 | 99.32 | *Talaromyces emersonii* | 591 | 591 |
| KR834708- AUZ02577 | 97.71 | *Talaromyces emersonii* | 595 | 568 |
| US20170306309-0023 | 94.57 | *Talaromyces sp* | 588 | 589 |
| WO2013189878-0024 | 94.42 | *Rasamsonia emersonii* | 617 | 591 |
| WO2014202616-31996 | 94.42 | *Rasamsonia emersonii* | 597 | 591 |
| CN103667212-BBF78214 | 72.44 | *Talaromyces funiculosus* | 616 | 595 |
| W00075296-0002 | 72.32 | *Thermoascus crustaceus* | 624 | 596 |

An alignment of the predicted mature sequences of FraGA1 (SEQ ID NO: 7); WcoGA1 (SEQ ID NO: 8); TeGA (SEQ ID NO: 9); AnGA (aa 25-640 of XP_001390530.1, SEQ ID NO: 10); TrGA (2VN4_A, SEQ ID NO: 11); KZT67263.1 (aa 19-571 of SEQ ID NO: 12); XP_002475369.1 (aa 18-569 of SEQ ID NO: 13); US20090325240-1847 (aa 17-570 of SEQ ID NO: 14); KZT09226.1 (aa 18-570 of SEQ ID NO: 15); WO2016196202-0012 (SEQ ID NO: 16); US20170314003-0002 (aa 19-575 of SEQ ID NO: 17); GAD95639.1 (aa 38-622 of SEQ ID NO: 18); US20170306309-0023 (SEQ ID NO: 19); and CAC28076.1 (aa 29-618 of SEQ ID NO: 20) was performed with default parameters using CLUSTALW software (Thompson et al., *Nucleic Acids Research*, 22:4673-4680, 1994). The multiple sequence alignment is shown on FIG. 1.

Example 11

Relative Activity of Glucoamylases at pH 1.9, 4.5 and 6.0

Glucose release from corn starch substrate was measured for the glucoamylases FraGA1 and WcoGA1 under conditions that mimicked those experienced in the ruminant digestive system. Each reaction mixture contained 0.1 mg of purified enzyme and 10% (w/v) corn starch (Sigma S-4126) in a 1 mL volume. For the pH 1.9 reactions, 0.1M glycine-HCl (pH 1.9) was used as diluent, and the reactions also contained 1000 units of porcine pepsin (Sigma P-7000). For the pH 4.5 reactions, the pH of 0.1M glycine was adjusted to 4.5 using 5N NaOH and pepsin was omitted. For the pH 6.0 reactions, 0.1M Mes-NaOH (pH6.0) was used as diluent and pepsin was omitted.

The reactions were carried out at 40° C. with shaking for 2 h. Samples were centrifuged to separate the supernatant and unreacted corn starch granules. The supernatant was heated at 99° C. for 10 min, filtered and 20 µl of filtrate was injected onto an HPLC using Na-Carbohydrate column to separate and quantify glucose generated using a glucose standard at 1 mg/mL.

The results of the reactions are shown in Table 13. The glucose release activity is expressed as mg glucose released per mL reaction. Both glucoamylases showed highest activity at pH4.5 relative to pH1.9 and 6.0. It was surprisingly found that both glucoamylases showed activity at pH1.9 in the presence of pepsin, and this activity at pH1.9 was more than 80% of the activity at pH6.0.

TABLE 13

Relative activity of Glucoamylases on corn starch substrate

| | FraGA1 | WcoGA1 |
|---|---|---|
| Activity at pH 1.9 with pepsin | 5.70 ± 0.08 | 4.40± |
| Activity at pH 4.5 | 13.27 ± 0.09 | 13.47 ± 0.16 |
| Activity at pH 6.0 | 4.48 ± 0.06 | 4.88 ± 0.11 |
| Ratio of activity at pH 1.9 vs pH 6.0 | 1.27 | 0.90 |

What is claimed is:

1. A recombinant host cell comprising a vector comprising a polynucleotide sequence that is at least 80% identical to the nucleotide sequence of SEQ ID NO: 4, 5 or 6, wherein the polynucleotide is operably linked to one or more control sequences that control the production of the encoded polypeptide in an expression host, and wherein said regulatory sequence is heterologous to the coding nucleotide sequence, or said regulatory sequence and coding sequence are not arranged as found together in nature.

2. The recombinant host cell of claim 1, which is a *Trichoderma, Aspergillus*, Myceliopthora or *Saccharomyces* cell.

3. The recombinant host cell of claim 1, which is an *E. coli, Bacillus, Streptomyces*, or *Pseudomonas* cell.

4. The recombinant host cell of claim 1, which is an ethanologenic microorganism.

5. The recombinant host cell of claim 1, which further expresses and secretes one or more additional enzymes selected from the group consisting of protease, hemicellulase, cellulase, peroxidase, lipolytic enzyme, metallo-lipolytic enzyme, xylanase, lipase, phospholipase, esterase, perhydrolase, cutinase, pectinase, pectate lyase, mannanase, keratinase, reductase, oxidase, phenoloxidase, lipoxygenase, ligninase, alpha-amylase, pullulanase, phytase, tannase, pentosanase, malanase, beta-glucanase, arabinosidase, hyaluronidase, chondroitinase, laccase, transferrase, and a combination thereof.

* * * * *